(12) United States Patent
Messana et al.

(10) Patent No.: US 8,609,881 B2
(45) Date of Patent: Dec. 17, 2013

(54) CURE ACCELERATORS FOR ANAEROBIC CURABLE COMPOSITIONS

(75) Inventors: Andrew Messana, Newington, CT (US); Anthony F. Jacobine, Meriden, CT (US); Steven Thomas Nakos, Andover, CT (US); David M. Glaser, New Britain, CT (US)

(73) Assignee: Henkel IP US LCC, Rocky Hill, CT (US)

( * ) Notice: Subject to any disclaimer, the term of this patent is extended or adjusted under 35 U.S.C. 154(b) by 706 days.

(21) Appl. No.: 12/116,500

(22) Filed: May 7, 2008

(65) Prior Publication Data

US 2009/0281335 A1    Nov. 12, 2009

(51) Int. Cl.
| | | |
|---|---|---|
| C07C 69/76 | (2006.01) | |
| C07C 303/00 | (2006.01) | |
| C07C 307/00 | (2006.01) | |
| C07C 309/00 | (2006.01) | |
| C07C 311/00 | (2006.01) | |
| C07C 315/00 | (2006.01) | |
| C07C 317/00 | (2006.01) | |
| C07C 321/00 | (2006.01) | |
| C07C 323/00 | (2006.01) | |
| C07C 381/00 | (2006.01) | |
| C07C 261/00 | (2006.01) | |
| C07C 269/00 | (2006.01) | |
| C07C 271/00 | (2006.01) | |
| C07C 69/74 | (2006.01) | |
| C07C 273/00 | (2006.01) | |
| C07C 275/00 | (2006.01) | |

(52) U.S. Cl.
USPC ........ 560/12; 560/8; 560/13; 560/16; 560/25; 560/128; 560/132; 564/50

(58) Field of Classification Search
None
See application file for complete search history.

(56) References Cited

U.S. PATENT DOCUMENTS

| | | |
|---|---|---|
| 3,218,305 A | 11/1965 | Krieble |
| 3,970,505 A | 7/1976 | Hauser et al. |
| 4,174,311 A | 11/1979 | Nakano et al. |
| 4,180,640 A | 12/1979 | Melody et al. |
| 4,259,462 A | 3/1981 | Nakano et al. |
| 4,287,330 A | 9/1981 | Rich |
| 4,321,349 A | 3/1982 | Rich |
| 5,411,988 A | 5/1995 | Bockow et al. |
| 5,605,999 A | 2/1997 | Chu et al. |
| 5,811,473 A | 9/1998 | Ramos et al. |
| 6,391,993 B1 | 5/2002 | Attarwala et al. |
| 6,583,289 B1 | 6/2003 | McArdle et al. |
| 6,835,762 B1 | 12/2004 | Kelmarczyk et al. |
| 6,897,277 B1 | 5/2005 | Klemarczyk et al. |
| 6,958,368 B1 | 10/2005 | Klemarczyk et al. |

FOREIGN PATENT DOCUMENTS

| | | |
|---|---|---|
| DE | 1817989 | 12/1976 |
| DE | 2806701 | 2/1978 |
| FR | 1581361 | 9/1969 |
| JP | 07-3008757 B | 12/1973 |
| JP | 02-292247 | 12/1990 |
| JP | 2004-277369 | 10/2004 |

OTHER PUBLICATIONS

Zlatanos et. al. Journal of the American Oil Chemists' Society, 1985, 62(11), 1575-1577.*
Perkin et al. Proceedings of the Chemical Society (1908), 24, 54; the Derwent abstract.*
JP-2004277369, 2004, p. 1-9 (a machine translation).*
R.D. Rich, "Anaerobic Adhesives", Handbook of Adhesive Technology, Chapter 39, pp. 761-774 (2003).
D.M. Young et al., "Polyesters from Lactones," Union Carbide F-40, p. 147.
International Search Report dated Jan. 6, 2010 in connection with International Patent Application No. PCT/US2009/042793 by the Korean Intellectual Property Office.
Bacherikov. B.A. et al., Reduction of acetophenone by sodium borohydride modified by diamides of L-tartaric acid, Ukrainskii Khimicheskii Zhurnal, 66(7-8) pp. 125-128 (2000)—see (2R,3R)-2,3-Dihydroxy-N,N'-bis(phenylamino)butanediamide (provided by KIPO).
Katritzky, Alan R. et al., "Chemistry of Benzotriazole. Preparation of 1,1-disubstituted hydrazines and their 2-acyl derivatives", Journal of the Chem. Soc., Perkin Transactions I: Organic and Bio-Organic Chemistry pp. 2297-2303 (1989)—see (2R,3R)-2,3-Dihydroxy-N,N'-bis(phenylamino)butanediamide (provided by KIPO).

* cited by examiner

*Primary Examiner* — Clinton Brooks
(74) *Attorney, Agent, or Firm* — Steven C. Bauman

(57) ABSTRACT

The present invention provides compound(s) selected from the group of compounds represented by structural Formula (I):

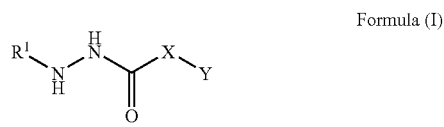

Formula (I)

wherein X, Y and $R^1$ are as described herein, use of such compounds as anaerobic cure accelerators, and compostions including such compounds.

22 Claims, 4 Drawing Sheets

US 8,609,881 B2

CURE ACCELERATORS FOR ANAEROBIC CURABLE COMPOSITIONS

BACKGROUND OF THE INVENTION

1. Field of the Invention

The present invention relates to novel cure accelerators that can be useful for anaerobic curable compositions, such as adhesives and sealants.

2. Brief Description of Related Technology

Anaerobic adhesive compositions generally are well-known. See e.g. R. D. Rich, "Anaerobic Adhesives" in *Handbook of Adhesive Technology* 29, 467-79, A. Pizzi and K. L. Mittal, eds., Marcel Dekker, Inc., New York (1994), and references cited therein. Their uses are legion and new applications continue to be developed.

Conventional anaerobic adhesives ordinarily include a free-radically polymerizable acrylate ester monomer, together with a peroxy initiator and an inhibitor component. Often, such anaerobic adhesive compositions also contain accelerator components to increase the speed with which the composition cures.

Desirable anaerobic cure-inducing compositions to induce and accelerate cure may include one or more of saccharin, toluidines, such as N,N-diethyl-p-toluidine ("DE-p-T") and N,N-dimethyl-o-toluidine ("DM-o-T"), acetyl phenylhydrazine ("APH"), maleic acid, and quinones, such as napthaquinone and anthraquinone. See, e.g., U.S. Pat. No. 3,218,305 (Krieble), U.S. Pat. No 4,180,640 (Melody), U.S. Pat. No 4,287,330 (Rich) and U.S. Pat. No 4,321,349 (Rich).

Saccharin and APH are used as standard cure accelerator components in anaerobic adhesive cure systems. The LOCTITE-brand anaerobic adhesive products currently available from Henkel Corporation use either saccharin alone or both saccharin and APH in most of its anaerobic adhesives. These components however have come under regulatory scrutiny in certain parts of the world, and thus efforts have been undertaken to identify candidates as replacements.

Examples of other curatives for anaerobic adhesives include thiocaprolactam (e.g., U.S. Pat. No. 5,411,988) and thioureas [e.g. U.S. Pat. No. 3,970,505 (Hauser) (tetramethyl thiourea), German Patent Document Nos. DE 1 817 989 (alkyl thioureas and N,N'-dicyclohexyl thiourea) and 2 806 701 (ethylene thiourea), and Japanese Patent Document No. JP 07-308,757 (acyl, alkyl, alkylidene, alkylene and alkyl thioureas)], certain of the latter of which had been used commercially up until about twenty years ago.

Loctite (R&D) Ltd. discovered a new class of materials— trithiadiaza pentatlenes—effective as curatives for anaerobic adhesive compositions. The addition of these materials into anaerobic adhesives as a replacement for conventional curatives (such as APH) surprisingly provides at least comparable cure speeds and physical properties for the reaction products formed therefrom. See U.S. Pat. No. 6,583,289 (McArdle).

U.S. Pat. No. 6,835,762 (Klemarczyk) provides an anaerobic curable composition based on a (meth)acrylate component with an anaerobic cure-inducing composition substantially free of acetyl phenylhydrazine and maleic acid and an anaerobic cure accelerator compound having the linkage —C(=O)—NH—NH— and an organic acid group on the same molecule, provided the anaerobic cure accelerator compound excludes 1-(2-carboxyacryloyl)-2-phenylhydrazine. The anaerobic cure accelerator is embraced by:

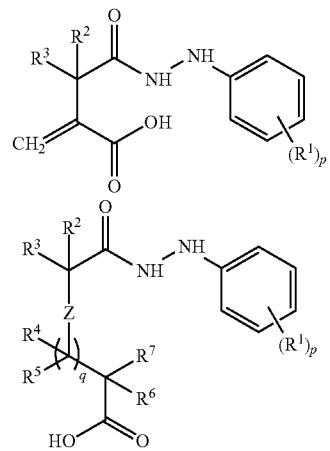

where $R^1$-$R^7$ are each independently selected from hydrogen and $C_{1-4}$; Z is a carbon-carbon single bond or carbon-carbon double bond; q is 0 or 1; and p is an integer between 1 and 5, examples of which are 3-carboxyacryloyl phenylhydrazine, methyl-3-carboxyacryloyl phenylhydrazine, 3-carboxypropanoyl phenylhydrazine, and methylene-3-carboxypropanoyl phenylhydrazine.

U.S. Pat. No. 6,897,277 (Klemarczyk) provides an anaerobic curable composition based on a (meth)acrylate component with an anaerobic cure-inducing composition substantially free of saccharin and an anaerobic cure accelerator compound within the following structure

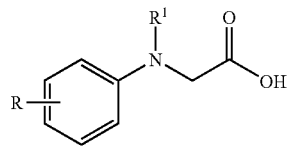

where R is selected from hydrogen, halogen, alkyl, alkenyl, hydroxyalkyl, hydroxyalkenyl, carboxyl, and sulfonato, and $R^1$ is selected from hydrogen, alkyl, alkenyl, hydroxyalkyl, hydroxyalkenyl, and aralkyl, an example of which is phenyl and N-methyl phenyl glycine.

U.S. Pat. No. 6,958,368 (Messana) provides an anaerobic curable composition. This composition is based on a (meth) acrylate component with an anaerobic cure-inducing composition substantially free of saccharin and within the following structure

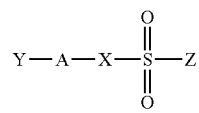

where Y is an aromatic ring, optionally substituted at up to five positions by $C_{1-6}$ alkyl or alkoxy, or halo groups; A is C=O, S=O or O=S=O; X is NH, O or S and Z is an aromatic ring, optionally substituted at up to five positions by $C_{1-6}$ alkyl or alkoxy, or halo groups, or Y and Z taken together may join to the same aromatic ring or aromatic ring system, provided that when X is NH, o-benzoic sulfimide is excluded from the structure. Examples of the anaerobic cure accelerator compound embraced by the structure above include 2-sulfobenzoic acid cyclic anhydride, and 3H-1,2-benzodithiol-3-one-1,1-dioxide.

Notwithstanding the state of the art, there is an on-going desire to find alternative technologies for anaerobic cure accelerators to differentiate existing products and provide supply assurances in the event of shortages or cessation of supply of raw materials. Moreover, since certain of the raw materials used in the anaerobic cure inducing composition have to one degree or another come under regulatory scrutiny, alternative components would be desirable. Accordingly, it would be desirable to identify new materials that function as cure components in the cure of anaerobically curable compositions.

SUMMARY OF THE INVENTION

In some non-limiting embodiments, the present invention provides compound(s) selected from the group of compounds represented by structural Formula (I):

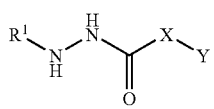

Formula (I)

wherein in Formula I: $R^1$ is selected from the group consisting of aryl and heteroaryl; X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X, wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH$_2$, and —SH, and provided that each of the —OH, —NH$_2$, -or —SH groups is not attached to the same carbon atom of Y or an —O—, —S—, or —NH— backbone moiety of Y.

In other embodiments, the present invention provides reaction product(s) prepared from reactants comprising: (a) at least one compound selected from the group of compounds represented by structural Formula (II):

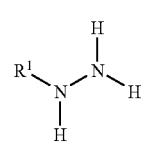

Formula (II)

wherein in Formula II: $R^1$ is selected from the group consisting of aryl and heteroaryl; and (b) at least one compound selected from the group of compounds represented by structural Formula (III) and structural Formula (IV):

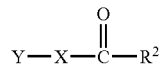

Formula (III)

wherein in Formula III: X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X, wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH$_2$, and —SH, and provided that each of the —OH, —NH$_2$, -or —SH groups is not attached to the same carbon atom of Y or an —O—, —S—, or —NH— backbone moiety of Y; and $R^2$ is selected from the group consisting of —OR, —NHR, alkyl, and arylalkyl, wherein R is H, alkyl or arylalkyl; and

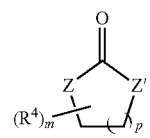

Formula (IV)

wherein in Formula IV: Z and Z' are each independently selected from the group consisting of —O—, —S—, and —N($R^3$)—, wherein $R^3$ is H or alkyl; m is at least 1; each $R^4$ is independently selected from the group consisting of hydroxyalkyl, aminoalkyl, thioalkyl, hydroxyl substituted cycloalkyl, arylalkyl having at least one —OH, —NH$_2$, or —SH group, and heteroarylalkyl having at least one —OH, —NH$_2$, or —SH group, provided that there is no more than one $R^4$ substituent attached to a substitutable ring carbon atom; and p is 1 or 2.

In other embodiments, the present invention provides reaction product(s) prepared from reactants comprising: (a) at least one compound selected from the group of compounds represented by structural Formula (V):

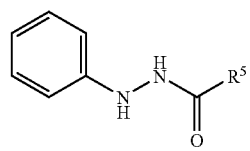

Formula (V)

wherein in Formula V: $R^5$ is selected from the group consisting of hydroxyalkyl and carboxyalkyl; and (b) at least one compound selected from the group of compounds represented by structural Formula (VI):

Formula (VI)

wherein in Formula VI: Z″ is selected from the group consisting of —O—, —S—, and —NH—; q is 1 to 4; $R^6$ is independently selected from the group consisting of hydroxyalkyl, aminoalkyl, and thioalkyl; and n is at least 1.

Compositions comprising the above compound(s) and reaction products also are provided.

In some non-limiting embodiments, the present invention provides method(s) of making a compound selected from the group of compounds represented by structural Formula (I):

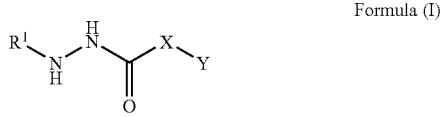

Formula (I)

wherein in Formula I: $R^1$ is selected from the group consisting of aryl and heteroaryl; X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms which optionally can be interrupted by an —O—, —S—, or —NH-moiety, provided that the —O—, —S—, or —NH— of Y, if present, is not adjacent to another —O—, —S—, or —NH— group of X, wherein the alkylene group has substituents which are independently selected from the group consisting of —OH, —$NH_2$, —SH, cycloalkyl, heterocyclyl, aryl, and heteroaryl, or two hydrogen atoms on the same carbon atom of Y are replaced by carbonyl, and wherein at least two substituents are each independently selected from the group consisting of —OH, —$NH_2$, and —SH, and provided that each of the —OH, —$NH_2$, -or —SH is not attached to the same carbon atom of Y or an —O—, —S—, or —NH— backbone moiety of Y, comprising the step of reacting:

(a) at least one compound selected from the group of compounds represented by structural Formula (II):

Formula (II)

wherein in Formula II: $R^1$ is selected from the group consisting of aryl and heteroaryl; with (b) at least one compound selected from the group of compounds represented by structural Formula (III) and structural Formula (IV):

Formula (III)

wherein in Formula III: X is selected from the group consisting of a direct bond, —O—, —S—, —NH—, alkylene, cycloalkylene, heterocyclylene, arylene, alkarylene, and heteroarylene; Y is a substituted alkylene group comprising an alkylene backbone having at least two contiguous carbon atoms which optionally can be interrupted by —O—, —S—, or —NH-moieties, provided that the —O—, —S—, or —NH— of Y, if present, is not adjacent to another —O—, —S—, or —NH— group of X, wherein the alkylene group has substituents which are independently selected from the group consisting of —OH, —$NH_2$, —SH, cycloalkyl, heterocyclyl, aryl, and heteroaryl, or two hydrogen atoms on the same carbon atom of Y are replaced by carbonyl, and wherein at least two substituents are each independently selected from the group consisting of —OH, —$NH_2$, and —SH, and provided that each of the —OH, —$NH_2$, -or —SH is not attached to the same carbon atom of Y or an —O—, —S—, or —NH— backbone moiety of Y; and $R^2$ is selected from the group consisting of —OR, NHR, alkyl, and arylalkyl, wherein R is H, alkyl or arylalkyl; and

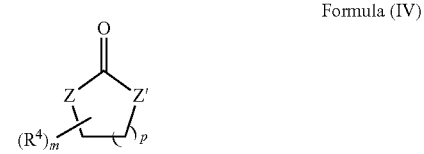

Formula (IV)

wherein in Formula IV: Z and Z′ are each independently selected from the group consisting of —O—, —S—, and —N($R^3$)—, wherein $R^3$ is H or alkyl; m is at least 1; each $R^4$ is independently selected from the group consisting of hydroxyalkyl, aminoalkyl, thioalkyl, hydroxyl substituted cycloalkyl, arylalkyl having at least one —OH, —$NH_2$, or —SH group, and heteroarylalkyl having at least one —OH, —$NH_2$, or —SH group, provided that there is no more than one $R^4$ substituent attached to a substitutable ring carbon atom; and p is 1 or 2.

BRIEF DESCRIPTION OF THE FIGURES

The foregoing summary, as well as the following detailed description, will be better understood when read in conjunction with the appended drawings. In the drawings.

DETAILED DESCRIPTION OF THE INVENTION

Figure 1:
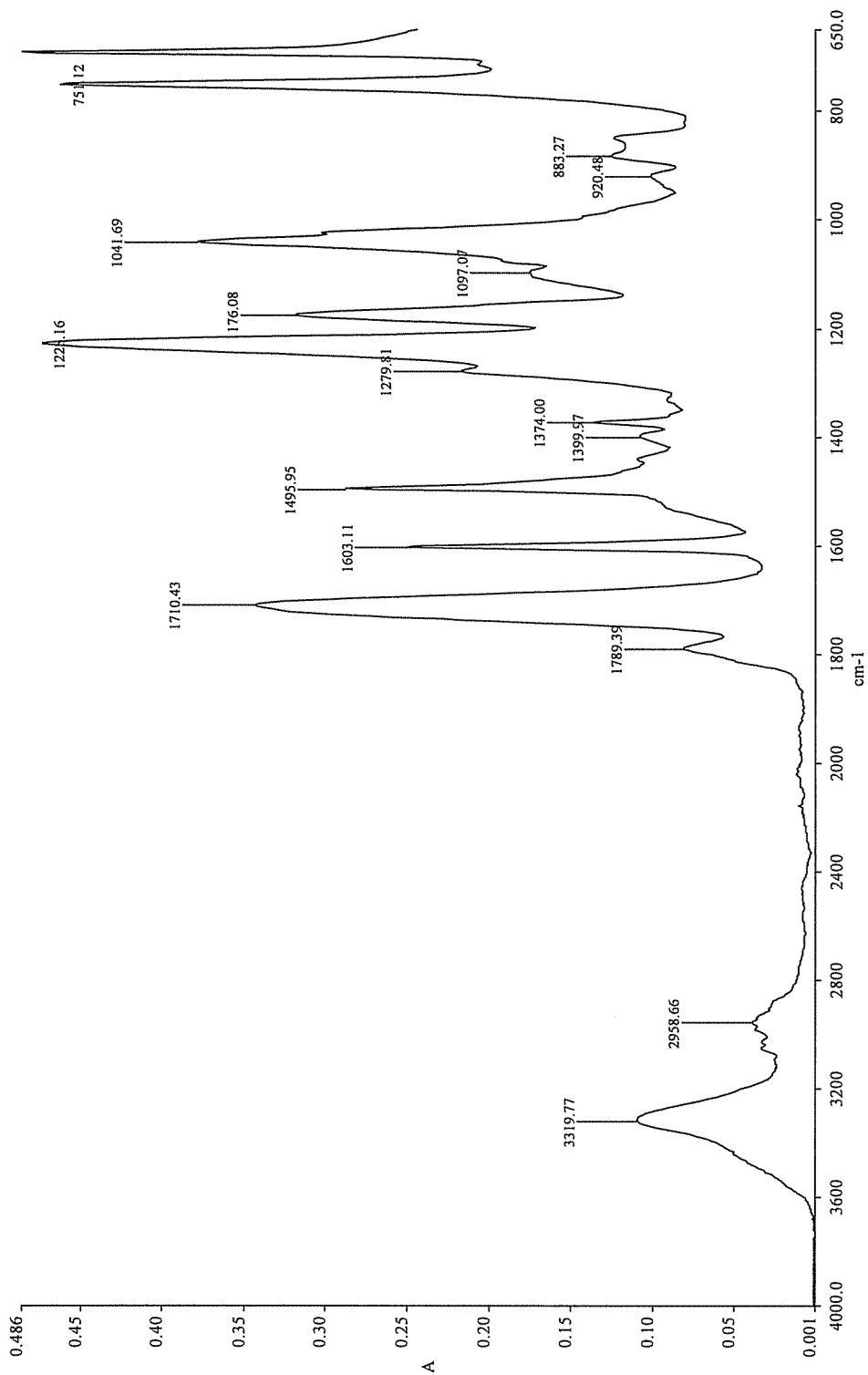
FIG. 1 depicts an IR spectra of a phenylhydrazine-glycerol carbonate reaction product of Example A according to the present invention.

Other than in the operating examples, or where otherwise indicated, all numbers expressing quantities of ingredients, thermal conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, the term "composition" is intended to encompass a product comprising the specified ingredients in the specified amounts, as well as any product which results, directly or indirectly, from combination of the specified ingredients in the specified amounts.

As used herein, "formed from" or "prepared from" denotes open, e.g., "comprising," claim language. As such, it is intended that a composition "formed from" or "prepared from" a list of recited components be a composition comprising at least these recited components or the reaction product of at least these recited components, and can further comprise other, non-recited components, during the composition's formation or preparation.

As used herein, the phrase "reaction product of" means chemical reaction product(s) of the recited components, and can include partial reaction products as well as fully reacted products.

As used herein, the term "polymer" in meant to encompass oligomers, and includes without limitation both homopolymers and copolymers. The term "prepolymer" means a compound, monomer or oligomer used to prepare a polymer, and includes without limitation both homopolymer and copolymer oligomers. The term "oligomer" means a polymer consisting of only a few monomer units up to about ten monomer units, for example a dimer, trimer or tetramer.

As used herein, the term "cure" as used in connection with a composition, e.g., "composition when cured" or a "cured composition", means that any curable or crosslinkable components of the composition are at least partially cured or crosslinked. In some non-limiting embodiments of the present invention, the chemical conversion of the crosslinkable components, i.e., the degree of crosslinking, ranges from about 5% to about 100% of complete crosslinking where complete crosslinking means full reaction of all crosslinkable components. In other non-limiting embodiments, the degree of crosslinking ranges from about 15% to about 80% or about 50% to about 60% of full crosslinking. One skilled in the art will understand that the presence and degree of crosslinking, i.e., the crosslink density, can be determined by a variety of methods, such as dynamic mechanical thermal analysis (DMA) using a TA Instruments DMA 2980 DMA analyzer over a temperature range of −65° F. (−18° C.) to 350° F. (177° C.) conducted under nitrogen according to ASTM D 4065-01. This method determines the glass transition temperature and crosslink density of free films of coatings or polymers. These physical properties of a cured material are related to the structure of the crosslinked network.

Curing of a polymerizable composition can be obtained by subjecting the composition to curing conditions, such as but not limited to heating, etc., leading to the reaction of reactive groups of the composition and resulting in polymerization and formation of a solid polymerizate. When a polymerizable composition is subjected to curing conditions, following polymerization and after reaction of most of the reactive groups occurs, the rate of reaction of the remaining unreacted reactive groups becomes progressively slower. In some non-limiting embodiments, the polymerizable composition can be subjected to curing conditions until it is at least partially cured. The term "at least partially cured" means subjecting the polymerizable composition to curing conditions, wherein reaction of at least a portion of the reactive groups of the composition occurs, to form a solid polymerizate. In some non-limiting embodiments, the polymerizable composition can be subjected to curing conditions such that a substantially complete cure is attained and wherein further exposure to curing conditions results in no significant further improvement in polymer properties, such as strength or hardness.

The present inventors have discovered compounds useful as cure accelerators for anaerobic compositions. The addition of such compounds as cure accelerators into anaerobic adhesives as a replacement for some or all of the amount of conventional anaerobic cure accelerators (such as toluidine, acetyl phenylhydrazine and/or cumene hydroperoxide) surprisingly provides at least comparable cure speeds and physical properties for the reaction products formed therefrom, as compared with those observed from conventional anaerobic curable compositions. As such, these materials provide many benefits to anaerobic adhesive compositions, including but not limited to: reduced odor and safety concerns, reduced bioavailability, good formulation stability and good solubility in anaerobic curable compositions.

As noted above, in some non-limiting embodiments the present invention provides compounds selected from the group of compounds represented by structural Formula (I):

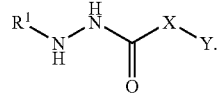

Formula (I)

In the compounds of Formula (I), $R^1$ is selected from the group consisting of aryl and heteroaryl.

As used herein, "aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Non-limiting examples of useful heteroaryls include those containing about 5 to about 6 ring atoms. The "heteroaryl" can be optionally substituted by one or more "ring system substituents" which may be the same or different, and are as defined herein. The prefix aza, oxa or thia before the heteroaryl root name means that at least one of a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The phrase "optionally substituted" means optional substitution with the specified groups, radicals or moieties.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, R$^2$, etc.) occurs more than one time in any constituent or in Formula I, etc., its definition on each occurrence is independent of its definition at every other occurrence.

In the compounds of Formula (I), X is selected from the group consisting of a direct bond, —O—, —S—, —NH—, alkylene, cycloalkylene, heterocyclylene, arylene, alkarylene, and heteroarylene. In some non-limiting embodiments, X is —O—.

As used herein, "alkylene" means a difunctional group obtained by removal of a hydrogen atom from an alkyl group such as is defined below. Non-limiting examples of alkylene groups include methylene, ethylene and propylene.

"Alkyl" means an aliphatic hydrocarbon group which may be straight or branched and comprising about 1 to about 20 carbon atoms in the chain, about 1 to about 12 carbon atoms in the chain, or about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Heterocyclene" means a difunctional group obtained by removal of a hydrogen atom from a heterocyclyl group such as is defined below. "Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like.

It should be noted that in heteroatom containing ring systems of this invention, there are no hydroxyl groups on carbon atoms adjacent to a N, O or S, as well as there are no N or S groups on carbon adjacent to another heteroatom. Thus, for example, in the ring:

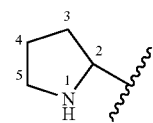

there is no —OH attached directly to carbons marked 2 and 5. It should also be noted that tautomeric forms such as, for example, the moieties:

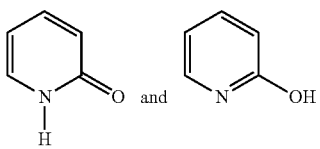 [SMILES: O=c1cccc[nH]1 ; "and" ; Oc1ccccn1]

are considered equivalent in certain embodiments of this invention.

"Arylene" means a difunctional group obtained by removal of a hydrogen atom from an aryl group such as is defined above.

"Alkarylene" means a difunctional group obtained by removal of a hydrogen atom from an alkaryl group such as is defined below. "Alkaryl" or "alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Heteroarylene" means a difunctional group obtained by removal of a hydrogen atom from a heteroaryl group such as is defined above.

In the compounds of Formula (I), Y is a substituted alkylene group comprising an alkylene backbone having at least two contiguous carbon atoms. The alkylene group Y optionally can be interrupted by one or more —O—, —S—, or —NH— moieties, provided that each —O—, —S—, or —NH— moiety of Y, if present, is not adjacent to an —O—, —S—, or —NH— of X. The alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl. As used herein, "cycloalkyl" means a non-aromatic mono- or multicyclic ring system comprising about 3 to about 10 carbon atoms, about 5 to about 10 carbon atoms, or about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

At least two substituents of Y are each independently selected from the group consisting of —OH, —NH$_2$, and —SH, provided that each of the —OH, —NH$_2$, -or —SH groups is not attached to the same carbon atom of Y or an —O—, —S—, or —NH— backbone moiety of Y. In some non-limiting embodiments, Y comprises two or three —OH substituents.

In some non-limiting embodiments, compound(s) of the present invention according to Formula (I) are represented by structural Formula I(a) below:

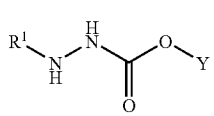

Formula (I(a))

wherein R$^1$ and Y are as described above.

In other embodiments, compounds of the present invention according to Formula (I) are represented by structural Formula I(b) and structural Formula I(c) as illustrated below:

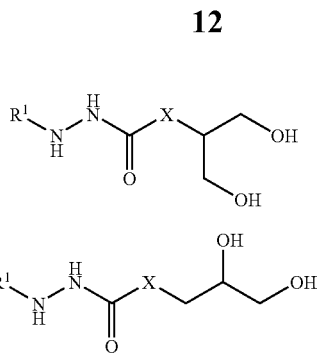

wherein X and R$^1$ are as described above.

In one embodiment, a compound of the present invention according to Formula (I) is represented by structural Formula (A):

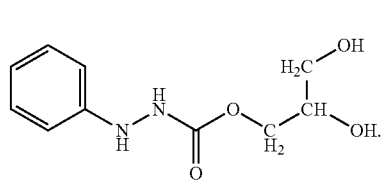

Formula (A)

In another embodiment, a compound of the present invention according to Formula (I) is represented by structural Formula (B):

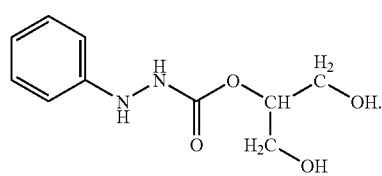

Formula (B)

In another embodiment, a compound of the present invention according to Formula (I) is represented by structural Formula (C):

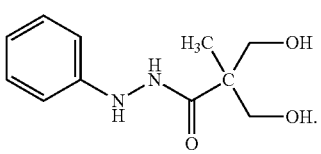

Formula (C)

In another embodiment, a compound of the present invention according to Formula (I) is represented by structural Formula (D):

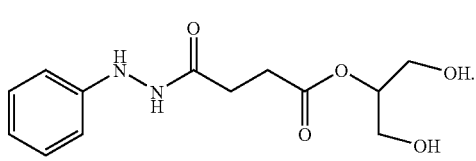

Formula (D)

Compounds of the present invention can be made by a variety of methods. In some non-limiting embodiments, the present invention provides reaction product(s) prepared from reactants comprising (1) at least one compound selected from the group of compounds represented by structural Formula (II)

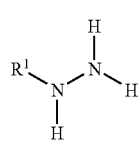
Formula (II)

and (2) at least one compound selected from the group of compounds represented by structural Formula (III) and structural Formula (IV):

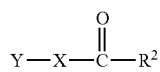
Formula (III)

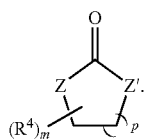
Formula (IV)

In Formula II above, $R^1$ is selected from the group consisting of aryl and heteroaryl. In some non-limiting embodiments, $R^1$ is phenyl. A non-limiting example of a suitable compound of Formula (II) is phenylhydrazine, represented by structural Formula II(a):

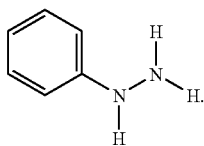
Formula (II(a))

In Formula III above, X is selected from the group consisting of a direct bond, —O—, —S—, —NH—, alkylene, cycloalkylene, heterocyclylene, arylene, alkarylene, and heteroarylene. In some non-limiting embodiments, X is —O—.

In Formula III, Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X. The alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl. At least two substituents of Y are each independently selected from the group consisting of —OH, —NH$_2$, and —SH, provided that each of the —OH, —NH$_2$, -or —SH groups is not attached to the same carbon atom of Y or an —O—, —S—, or —NH— backbone moiety of Y. $R^2$ is selected from the group consisting of —OH, —OR, NHR, alkyl, and arylalkyl, wherein R is an alkyl or an arylalkyl group. In some non-limiting embodiments, Y comprises two or three —OH substituents.

In some non-limiting embodiments, compound(s) of Formula (III) can be represented by Formulae (III(a)), (III(b)) or (III(c)):

Formula (III(a))

Formula (III(b))

Formula (III(c))

In Formula IV above, Z and Z' are each independently selected from the group consisting of —O—, —S—, and —N(R$^3$), wherein $R^3$ is H or alkyl. The variable m is at least 1. In some non-limiting embodiments, m is 1 or 2. Each $R^4$ is independently selected from the group consisting of hydroxyalkyl, aminoalkyl, thioalkyl, hydroxyl substituted cycloalkyl, arylalkyl having at least one —OH, —NH$_2$, or —SH group pendant from the alkyl group or the aryl group of the arylalkyl, and heteroarylalkyl having at least one —OH, —NH$_2$, or —SH group pendant from the alkyl group or the aryl group of the heteroarylalkyl. In some non-limiting embodiments, $R^4$ is hydroxyalkyl. The variable can be 1 or 2.

In some non-limiting embodiments, compound(s) of Formula (IV) can be represented by structural Formulae (IV(a)) or (IV(b)):

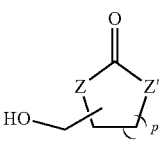
Formula (IV(a))

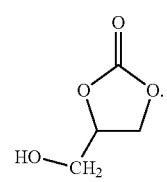
Formula (IV(b))

In some non-limiting embodiments, the reaction product is prepared from phenylhydrazine and one or more of the above compounds of Formulae (III(b)), (III(c)) and/or (IV(b)).

In some non-limiting embodiments, the reaction product is prepared from phenylhydrazine and glycerol carbonate as shown in the reaction scheme below:

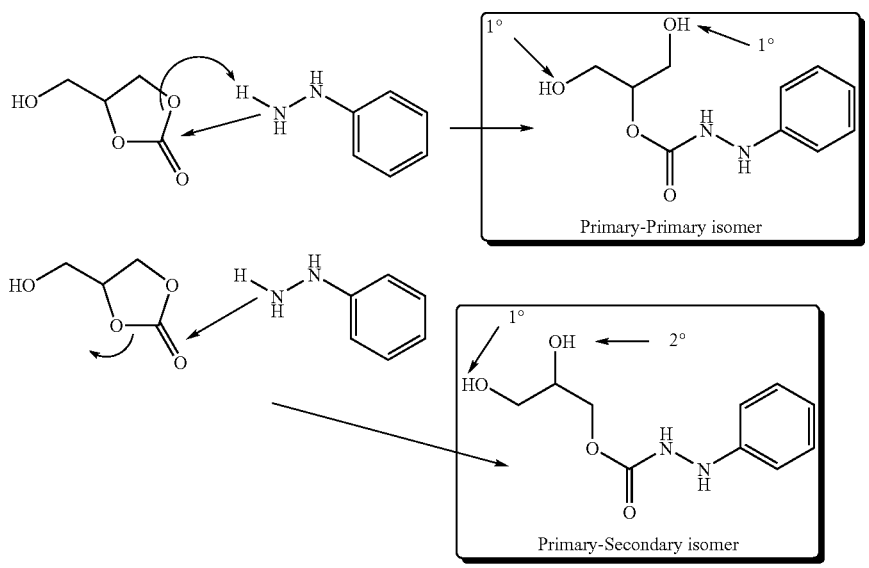

In some non-limiting embodiments, there may be minor amounts of residual reactants, such as phenylhydrazine and glycerol carbonate, present with the final reaction product(s), for example less than about 5 weight percent, or less than about 1 weight percent, or free of residual reactants, based upon total weight of the reaction products and any residual reactants.

In another non-limiting embodiment, the reaction product is prepared from phenylhydrazine and dimethylol propionic acid as shown in the reaction scheme below:

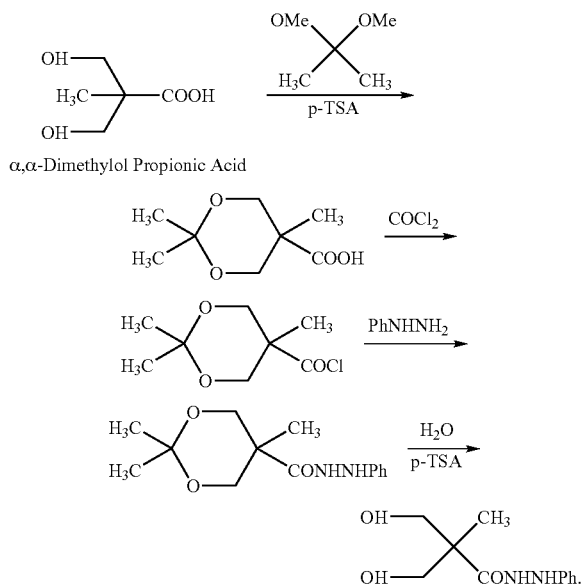

In another non-limiting embodiment, the reaction product is prepared from phenylhydrazine and tartaric acid as shown in the reaction scheme below:

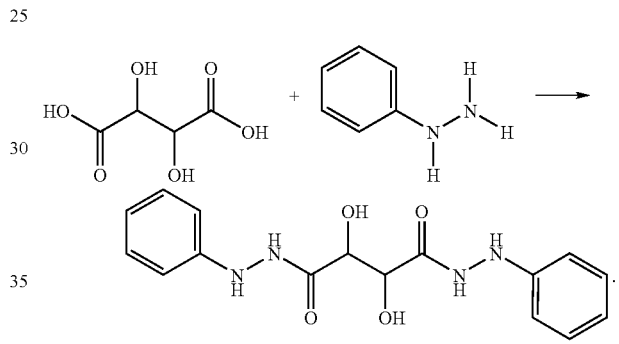

In some non-limiting embodiments, the molar ratio of compound(s) of Formula (II) to compound(s) of Formulae (III) and/or (IV) can range from about 5:1 to about 1:5, or about 3:1 to about 1:3, or about 1:1.

In some non-limiting embodiments, the reaction is conducted in the presence of a solvent. In some non-limiting embodiments, the compound of Formula (IV) is dissolved in solvent prior to reaction with the compound of Formula (II). Nonlimiting examples of suitable solvents include, but are not limited to, mineral spirits, alcohols such as methanol, ethanol or butanol, aromatic hydrocarbons such as xylene, glycol ethers such as ethylene glycol monobutyl ether, esters, aliphatics, and mixtures of any of the foregoing. In some embodiments, residual solvent is extracted from the reaction product(s), for example by distillation or chromatography.

In some non-limiting embodiments, the reaction product(s) are purified to remove impurities, such as reaction by-products or impurities that accompany the reactants such as carriers. The reaction product(s) can be purified for example by filtration, stripping or chromatography, such that the purified reaction product(s) are essentially free of impurities, or comprise less than about 1 weight percent of impurities, or are free of impurities.

In some non-limiting embodiments, the reaction product may be a compound of Formula (I), for example compounds represented by Formula (A) or Formula (B), or alternatively a mixture of compounds of Formula (I), for example a mixture of a compound represented by Formula (A) and a compound represented by structural Formula (B).

In other embodiments, the present invention provides reaction products prepared from reactants comprising at least one compound selected from the group of compounds represented by structural Formula (V):

Formula (V)

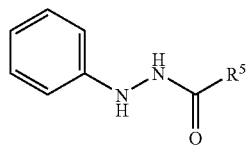

and at least one compound selected from the group of compounds represented by structural Formula (VI):

Formula (VI)

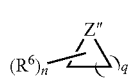

In Formula V, $R^5$ is selected from the group consisting of hydroxyalkyl and carboxyalkyl. In one embodiment of the present invention, the reactant represented by Formula (V) is:

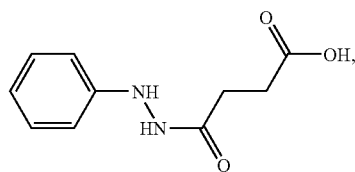

("SPH"), which is the reaction product of succinic anhydride and phenyl hydrazine and can be prepared according to U.S. Pat. No. 6,835,762, incorporated by reference herein.

In Formula VI, Z" is selected from the group consisting of —O—, —S—, and —NH—; q may be 1 to 4; $R^6$ may be independently selected from the group consisting of hydroxyalkyl, aminoalkyl, and thioalkyl; and n is at least 1. In another embodiment the reactant represented by Formula (VI) is

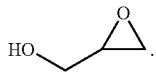

In another non-limiting embodiment, the reaction product is prepared from SPH and glycidol as shown in the reaction scheme below:

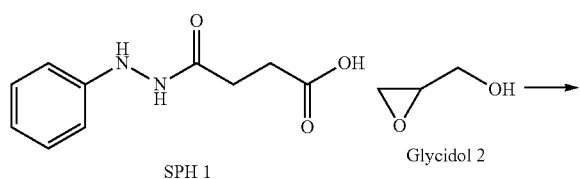

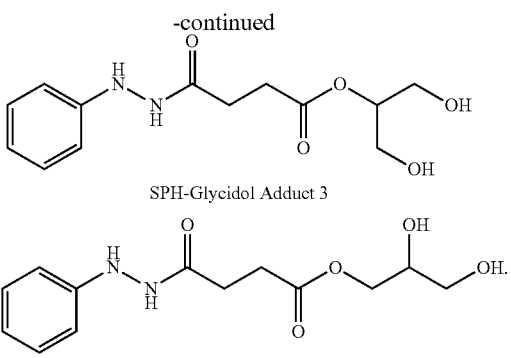

SPH-Glycidol Adduct 3

In some embodiments, reaction products of the above reactants SPH and glycidol can be represented by structural Formula (D1) and/or (D2):

Formula (D1)

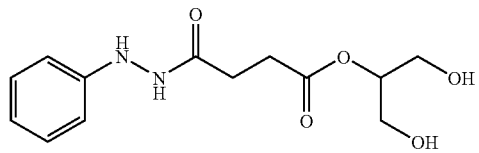

Formula (D2)

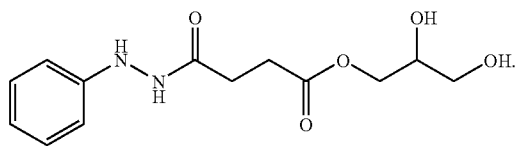

In some non-limiting embodiments, the molar ratio of compound(s) of Formula (V) to compound(s) of Formulae (VI) can range from about 5:1 to about 1:5, or about 3:1 to about 1:3, or about 1:1.

In some non-limiting embodiments, the reaction of compounds of Formula (V) and (VI) is conducted in the presence of a solvent. Suitable solvents and amounts are discussed in detail above.

In some non-limiting embodiments, the present invention provides methods of making compound(s) selected from the group of compounds represented by Formula (I):

Formula (I)

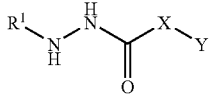

by reacting at least one compound selected from the group of compounds represented by Formula (II):

Formula (II)

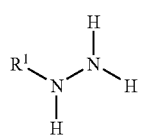

with at least one compound selected from the group of compounds represented by Formula (III) and Formula (IV):

Formula (III)

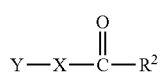

Formula (IV)

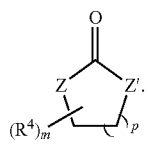

The reaction of compound(s) of Formula (II) and compound(s) of Formulae (III) and/or (IV) can be carried out in the presence of a solvent as discussed above. In some non-limiting embodiments, the compound(s) of Formulae (I) and/or (IV) can be solubilized in the solvent. The compound(s) of Formula (II) can be added to the mixture, allowed to exotherm and, if needed, heated at a temperature of about 0° C. to about 60° C., or about 60° C., for about 2 hours to about 7 days. The solvent can be removed by vacuum, if desired, for example at a temperature of about 60° C. and 100 torr and cooled, if desired.

Anaerobic curable compositions generally are based on a (meth)acrylate component, together with an anaerobic cure-inducing composition. In some non-limiting embodiments, the anaerobic curable composition of the present invention is based on the (meth)acrylate component, together with an anaerobic cure-inducing composition which preferably has at least reduced levels of APH (such as about 50% or less by weight of that which is used in conventional anaerobic curable compositions), is substantially free of APH (less than about 10 weight percent, less than about 5 weight percent or less than about 1 weight percent) or is free of APH. In place of some or all of APH is the inventive cure accelerator, such as compounds of Formula I or the above reaction products.

(Meth)acrylate monomers suitable for use as the (meth)acrylate component in the present invention may be selected from a wide variety of materials, such as those represented by $H_2C=CGCO_2R^8$, where G may be hydrogen, halogen or alkyl groups having from 1 to about 4 carbon atoms, and $R^8$ may be selected from alkyl, cycloalkyl, alkenyl, cycloalkenyl, alkaryl, aralkyl or aryl groups having from 1 to about 16 carbon atoms, any of which may be optionally substituted or interrupted as the case may be with silane, silicon, oxygen, halogen, carbonyl, hydroxyl, ester, carboxylic acid, urea, urethane, carbonate, amine, amide, sulfur, sulfonate, sulfone and the like.

Additional (meth)acrylate monomers suitable for use herein include polyfunctional (meth)acrylate monomers, for example di-or tri-functional (meth)acrylates such as polyethylene glycol di(meth)acrylates, tetrahydrofuran (meth)acrylates and di(meth)acrylates, hydroxypropyl(meth)acrylate ("HPMA"), hexanediol di(meth)acrylate, trimethylol propane tri(meth)acrylates ("TMPTMA"), diethylene glycol dimethacrylate, triethylene glycol dimethacrylates ("TRIEGMA"), tetraethylene glycol di(meth)acrylates, dipropylene glycol di(meth)acrylates, di-(pentamethylene glycol) di(meth)acrylates, tetraethylene diglycol di(meth)acrylates, diglycerol tetra(meth)acrylates, tetramethylene di(meth) acrylates, ethylene di(meth)acrylates, neopentyl glycol di(meth)acrylates, and bisphenol-A mono and di(meth)acrylates, such as ethoxylated bisphenol-A (meth)acrylate ("EBIPMA"), and bisphenol-F mono and di(meth)acrylates, such as ethoxylated bisphenol-A (meth)acrylate.

Still other (meth)acrylate monomers that may be used herein include silicone (meth)acrylate moieties ("SiMA"), such as those taught by and claimed in U.S. Pat. No. 5,605,999 (Chu), incorporated herein by reference.

Other suitable monomers include polyacrylate esters represented by the formula

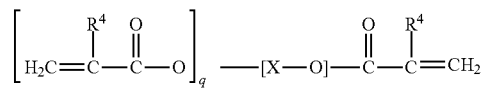

wherein $R^4$ is a radical selected from the group consisting of hydrogen, halogen and alkyl of from 1 to about 4 carbon atoms; q is an integer equal to at least 1, and preferably equal to from 1 to about 4; and X is an organic radical containing at least two carbon atoms and having a total bonding capacity of q plus 1. With regard to the upper limit for the number of carbon atoms in X, workable monomers exist at essentially any value. As a practical matter, however, a general upper limit is about 50 carbon atoms, preferably 30, and most preferably about 20.

For example, X can be an organic radical of the formula:

wherein each of $Y^1$ and $Y^2$ is an organic radical, preferably a hydrocarbon group, containing at least 2 carbon atoms, and preferably from 2 to about 10 carbon atoms, and Z is an organic radical, preferably a hydrocarbon group, containing at least 1 carbon atom, and preferably from 2 to about 10 carbon atoms.

Other classes of useful monomers are the reaction products of di- or tri-alkylolamines (e.g., ethanolamines or propanolamines) with acrylic acids, such as are disclosed in French Pat. No. 1,581,361.

Non-limiting examples of useful acrylic ester oligomers include those having the following general formula:

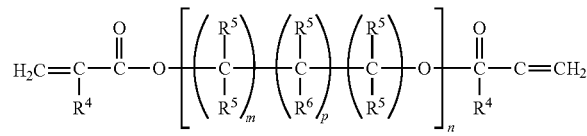

wherein $R^5$ represents a radical selected from the group consisting of hydrogen, lower alkyl of from 1 to about 4 carbon atoms, hydroxy alkyl of from 1 to about 4 carbon atoms, and

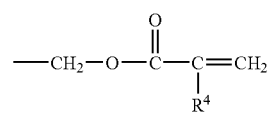

wherein $R^4$ is a radical selected from the group consisting of hydrogen, halogen, and lower alkyl of from 1 to about 4 carbon atoms; $R^6$ is a radical selected from the group consisting of hydrogen, hydroxyl, and

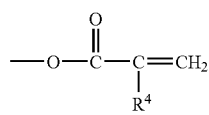

m is an integer equal to at least 1, e.g., from 1 to about 15 or higher, and preferably from 1 to about 8; n is an integer equal to at least 1, e.g., 1 to about 40 or more, and preferably between about 2 and about 10; and p is 0 or 1.

Typical examples of acrylic ester oligomers corresponding to the above general formula include di-, tri- and tetraethyleneglycol dimethacrylate; di(pentamethyleneglycol) dimethacrylate; tetraethyleneglycol diacrylate; tetraethyleneglycol di(chloroacrylate); diglycerol diacrylate; diglycerol tetramethacrylate; butyleneglycol dimethacrylate; neopentylglycol diacrylate; and trimethylolpropane triacrylate.

While di- and other polyacrylate esters, and particularly the polyacrylate esters described in the preceding paragraphs, can be desirable, monofunctional acrylate esters (esters containing one acrylate group) also may be used. When dealing with monofunctional acrylate esters, it is highly preferable to use an ester which has a relatively polar alcoholic moiety. Such materials are less volatile than low molecular weight alkyl esters and, more important, the polar group tends to provide intermolecular attraction during and after cure, thus producing more desirable cure properties, as well as a more durable sealant or adhesive. Most preferably, the polar group is selected from the group consisting of labile hydrogen, heterocyclic ring, hydroxy, amino, cyano, and halo polar groups. Typical examples of compounds within this category are cyclohexyl methacrylate, tetrahydrofurfuryl methacrylate, hydroxyethyl acrylate, hydroxypropyl methacrylate, t-butylaminoethyl methacrylate, cyanoethylacrylate, and chloroethyl methacrylate.

Another useful class of monomers is prepared by the reaction of a monofunctionally substituted alkyl or aryl acrylate ester containing an active hydrogen atom on the functional substituent. This monofunctional, acrylate-terminated material is reacted with an organic polyisocyanate in suitable proportions so as to convert all of the isocyanate groups to urethane or ureido groups. The monofunctional alkyl and aryl acrylate esters are preferably the acrylates and methacrylates containing hydroxy or amino functional groups on the nonacrylate portion thereof. Acrylate esters suitable for use have the formula

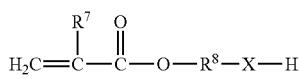

wherein X is selected from the group consisting of —O— and

and $R^9$ is selected from the group consisting of hydrogen and lower alkyl of 1 through 7 carbon atoms, $R^7$ is selected from the class consisting of hydrogen, chlorine and methyl and ethyl radicals; and $R^8$ is a divalent organic radical selected from the group consisting of lower alkylene of 1 through 8 carbon atoms, phenylene and naphthylene. These groups upon proper reaction with a polyisocyanate, yield a monomer of the following general formula:

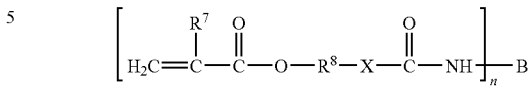

wherein n is an integer from 2 to about 6; B is a polyvalent organic radical selected from the group consisting of alkyl, alkenyl, cycloalkyl, cycloalkenyl, aryl, aralkyl, alkaryl and heterocyclic radicals both substituted and unsubstituted; and $R^7$, $R^8$ and X have the meanings given above.

The hydroxy- and amine-containing materials suitable for use in the preparation of the above monomeric products are exemplified by, but not limited to, such materials as hydroxyethyl acrylate, hydroxyethyl methacrylate, aminoethyl methacrylate, 3-hydroxypropyl methacrylate, aminopropyl methacrylate, hydroxyhexyl acrylate, t-butylaminoethyl methacrylate, hydroxyoctyl methacrylate, and the like.

The preferred organic polyisocyanates comprise the higher alkenyl diisocyanates, the cycloalkenyl diisocyanates and the aromatic diisocyanates containing 8 or more carbon atoms and preferably from 8 to about 30 carbon atoms, such as, for example, octamethylene diisocyanate, durene diisocyanate, 4,4'-diphenyldiisocyanate, and toluene diisocyanate.

The proportions in which the reactants may be combined can be varied somewhat; however, it is generally preferred to employ the reactants in chemically equivalent amounts up to a slight excess, e.g., 1 equivalent excess of the polyisocyanate. As used herein the expression "chemically equivalent amount" refers to the amount needed to furnish one isocyanate group per hydroxy or amino group.

The reaction may be accomplished in the presence or absence of diluents. Preferably diluents which include the hydrocarbons, such as aliphatic, cycloaliphatic and aromatic hydrocarbons, for example, benzene, toluene, cyclohexane, hexane, heptane and the like, are employed but other diluents, such as methyl isobutyl ketone, diamyl ketone, isobutyl methacrylate, triethyleneglycol dimethacrylate, and cyclohexyl methacrylate can also be beneficially utilized, if desired, especially where complete compatibility with the sealant system is desired.

The temperature employed in the reaction may also vary over a wide range. Where the components are combined in approximately chemical equivalent amounts or with slight excess of the isocyanate reactant, useful temperatures may vary from room temperature or below, e.g., 10° C. to 15° C., up to and including temperatures of 100° C. to 175° C. Where reacting the simpler isocyanates, the components are preferably combined at or near room temperature, such as temperatures ranging from 20° C. to 30° C. In the preparation of the high molecular weight isocyanate adducts using an excess of the isocyanate, the reactants may be combined at room temperature or preferably heated at temperatures ranging from about 40° C. to about 150° C. Reactions conducted at about 90° C. to 120° C. have been found to proceed quite smoothly.

Of course, combinations of these (meth)acrylate monomers may also be used.

The (meth)acrylate component can comprise from about 10 to about 90 percent by weight of the composition, such as about 60 to about 90 percent by weight, based on the total weight of the composition.

Recently, additional components have been included in traditional anaerobic adhesives to alter the physical properties of either the formulation or the reaction products thereof. For instance, one or more of maleimide components, thermal resistance-conferring coreactants, diluent components reactive at elevated temperature conditions, mono- or poly-hydroxyalkanes, polymeric plasticizers, and chelators (see U.S. Pat. No. 6,391,993, incorporated herein by reference) may be included to modify the physical property and/or cure profile of the formulation and/or the strength or temperature resistance of the cured adhesive.

When used, the maleimide, coreactant, reactive diluent, plasticizer, and/or mono- or poly-hydroxyalkanes, may be present in an amount within the range of about 1 percent to about 30 percent by weight, based on the total weight of the composition.

The inventive compositions may also include other conventional components, such as free radical initiators, free radical co-accelerators, and inhibitors of free radical generation, as well as metal catalysts.

A number of well-known initiators of free radical polymerization are typically incorporated into the inventive compositions including, without limitation, hydroperoxides, such as cumene hydroperoxide ("CHP"), para-menthane hydroperoxide, t-butyl hydroperoxide ("TBH") and t-butyl perbenzoate. Other peroxides include benzoyl peroxide, dibenzoyl peroxide, 1,3-bis(t-butylperoxyisopropyl)benzene, diacetyl peroxide, butyl 4,4-bis(t-butylperoxy)valerate, p-chlorobenzoyl peroxide, t-butyl cumyl peroxide, t-butyl perbenzoate, di-t-butyl peroxide, dicumyl peroxide, 2,5-dimethyl-2,5-di-t-butylperoxyhexane, 2,5-dimethyl-2,5-di-t-butyl-peroxyhex-3-yne, 4-methyl-2,2-di-t-butylperoxypentane and combinations thereof.

Such peroxide compounds are typically employed in the present invention in the range of from about 0.1 to about 10 percent by weight, based on the total weight of the composition, with about 1 to about 5 percent by weight being desirable.

As noted, conventional accelerators of free radical polymerization may also be used in conjunction with the inventive anaerobic cure accelerators, though in amounts less than that used in the past. Such accelerators are typically of the hydrazine variety (e.g., APH), as disclosed in U.S. Pat. No. 4,287,350 (Rich) and U.S. Pat. No. 4,321,349 (Rich). Maleic acid is usually added to APH-containing anaerobic cure systems. One benefit of the present invention is that the inventive anaerobic cure accelerators render the use of such acids unnecessary in preparing anaerobic adhesive compositions.

Co-accelerators of free radical polymerization may also be used in the compositions of the present invention including, without limitation, organic amides and imides, such as benzoic sulfimide (also known as saccharin) (See U.S. Pat. No. 4,321,349).

Stabilizers and inhibitors (such as phenols including hydroquinone and quinones) may also be employed to control and prevent premature peroxide decomposition and polymerization of the composition of the present invention, as well as chelating agents [such as the tetrasodium salt of ethylenediamine tetraacetic acid ("EDTA")] to trap trace amounts of metal contaminants therefrom. When used, chelating agents may ordinarily be present in the compositions in an amount from about 0.001 percent by weight to about 0.1 percent by weight, based on the total weight of the composition.

The inventive anaerobic cure accelerators may be used in amounts of about 0.1 to about 5 percent by weight, such as about 1 to about 2 percent by weight, based on the total weight of the composition. When used in combination with conventional accelerators (though at lower levels than such conventional accelerators), the inventive accelerators should be used in amounts of 0.01 to 5 percent by weight, such as 0.02 to 2 percent by weight, based on the total weight of the composition.

Metal catalyst solutions or pre-mixes thereof are used in amounts of about 0.03 to about 0.1 percent by weight.

Other additives such as thickeners, non-reactive plasticizers, fillers, toughening agents (such as elastomers and rubbers) and other well-known additives may be incorporated therein where the art-skilled believes it would be desirable to do so.

The present invention also provides methods of preparing and using the inventive anaerobic adhesive compositions, as well as reaction products of the compositions.

The compositions of the present invention may be prepared using conventional methods which are well known to those persons of skill in the art. For instance, the components of the inventive compositions may be mixed together in any convenient order consistent with the roles and functions the components are to perform in the compositions. Conventional mixing techniques using known apparatus may be employed.

The compositions of this invention may be applied to a variety of substrates to perform with the desired benefits and advantages described herein. For instance, appropriate substrates may be constructed from steel, brass, copper, aluminum, zinc, and other metals and alloys, ceramics and thermosets. The compositions of this invention demonstrate particularly good bond strength on steel, brass, copper and zinc. An appropriate primer for anaerobic curable compositions may be applied to a surface of the chosen substrate to enhance cure rate. Or, the inventive anaerobic cure accelerators may be applied to the surface of a substate as a primer. See e.g. U.S. Pat. No. 5,811,473 (Ramos).

In addition, the invention provides a method of preparing an anaerobic curable composition, a step of which includes mixing together a (meth)acrylate component, an anaerobic cure inducing composition comprising an anaerobic cure accelerator compound of Formula (I) or a reaction product as discussed above.

The invention also provides a process for preparing a reaction product from the anaerobic curable composition of the present invention, the steps of which include applying the composition to a desired substrate surface and exposing the composition to an anaerobic environment for a time sufficient to cure the composition.

This invention also provides a method of using as a cure accelerator for anaerobic curable composition, compound of Formula (I) or a reaction product as discussed above.

And the present invention provides a method of using an anaerobic cure accelerator compound, including (I) mixing the anaerobic cure accelerator compound in an anaerobic curable composition or (II) applying onto a surface of a substrate the anaerobic cure accelerator compound and applying thereover an anaerobic curable composition. Of course, the present invention also provides a bond formed between mated substrates with the inventive composition.

In view of the above description of the present invention, it is clear that a wide range of practical opportunities are provided. The following examples are illustrative purposes only, and are not to be construed so as to limit in any way the teaching herein.

EXAMPLES

I. Synthesis of Phenylhydrazine-Glycerol Carbonate (PHGC) Reaction Products

An investigation was performed to evaluate phenylhydrazine-glycerol carbonate reaction products as replacements for APH cure accelerator, for example, in anaerobic curable compositions, such as adhesives.

The inventive anaerobic cure accelerators were prepared in accordance with the synthetic scheme depicted below:

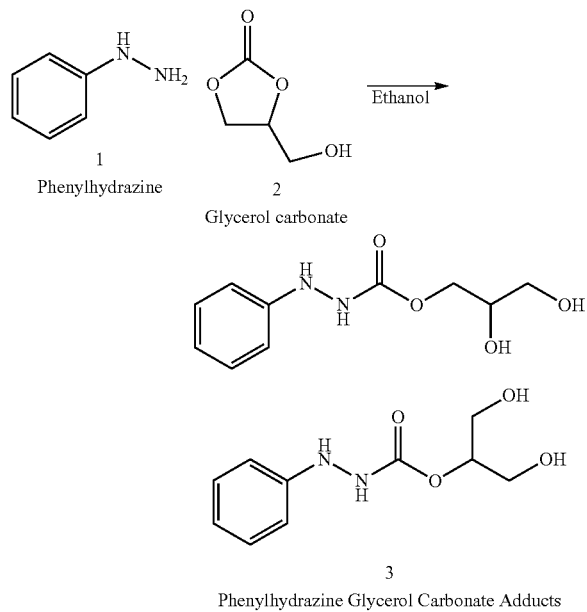

Phenylhydrazine Glycerol Carbonate Adducts

Phenylhydrazine and glycerol carbonate were reacted in the presence of ethanol in amounts and the manner described below to form PHGC reaction products (adducts) as as shown in Table 1:

TABLE 1

Reagents and Materials:

| Reagent | Phenylhydrazine | Glycerol Carbonate | Ethanol | Adducts |
|---|---|---|---|---|
| Supplier | Aldrich | Ube Ind. | — | — |
| C.A.S. No. | 100-63-0 | 931-40-8 | 64-17-5 | — |
| Molecular Weight (g/mole) | 108.14 | 118.09 | 46.07 | 226.23 |
| % Active | 97 | est* 93.5% | — | — |
| Melting point (° C.) | 18-21 | — | — | — |
| Boiling point (° C.) | 238-241 | — | 78 | — |
| Density g/ml | 1.099 | — | 0.789 | — |
| | | | | Theoretical Yield |
| Amount (g) | 50.00 | 59.50 | 100 ml | 101.5 |
| mmols | 448.50 | 471.00 | | 448.50 |

*Estimated 93.5% based on Huntsmann MSDS.

Example A

To a 3 necked, 500 ml round-bottomed flask equipped with magnetic stirring, a reflux condenser, pressure equilibrated addition funnel, nitrogen purge and thermo-probe was added phenylhydrazine (liquid 1) (50.0 g, 448.5 mmol) followed by ethanol (50 ml). To this clear solution was added a solution of glycerol carbonate (liquid 2) (59.5 g, 471.0 mmol) and the solvent ethanol (50 ml). This was added over 30 minutes at room temperature (about 25° C.), whereby the mixture remained clear with a minimal exotherm. The mixture was warmed to 70° C. and allowed to stir overnight. The temperature was raised the following day to a gentle reflux of 78° C. After five days, an aliquot was analyzed by FT-IR. It appeared by IR that more progress was made. The reaction was ended.

The reaction mixture was concentrated in vacuo (about 60° C. and 100 Torr) to a pale amber oil. This oil was further concentrated in vacuo (about 60° C. and 10 Torr) to a pale amber viscous oil/solids (113.01 g; 111.3% of theoretical yield). It was believed that this sample still contained residual ethanol since the weight exceeded the calculated yield. The oil was placed in a refrigerator at a temperature of about 10° C.

It was observed that phenylhydrazine has limited solubility in water (~10% by weight) and the glycerol carbonate appeared very soluble in water. A small amount of the above reaction product (~10 g) was re-dissolved in ethyl acetate (100 ml) and washed with water (100 ml). The organic portion was separated and dried with anhydrous $MgSO_4$, gravity filtered and then concentrated in vacuo to an oil (5.1 grams, 51 weight % recovery). The oil was placed in a refrigerator at a temperature of about 10° C. The material was further dried in vacuo at about 100 mTorr and 50° C. to provide Sample A. The solid was analyzed by FT-IR, $^1H$ NMR and $^{13}C$ NMR. Proton Nuclear Magnetic Resonance analyses were performed using a Varian 300 MHz Gemini Spectrophotometer. Melting points were obtained on a TA Instrument 2920 Differential Scanning Calorimeter.

FIG. 1 provides the result of an FT-IR analysis of PHGC reaction product Sample A. The results clearly show that nearly all anhydride was consumed. $^1H$ NMR: (DMSO-d6, 300 MHz) δ 9.0, 7.65, 7.15, 6.6, 5.2-3.35, 2.0. $^{13}C$ NMR: (DMSO-d6, 75 MHz) δ 157.5, 150.0, 129.5, 119.5, 112.5, 74.0, 67.5, and 66.5.

Example B

Phenylhydrazine (50.0 g, 0.462 mol) was mixed with glycerol carbonate (54.6 g, 0.462 mol) at room temperature (about 25° C.). An exotherm to 35° C. was observed within about 5 minutes. FT-IR indicated C=O shift from 1762 $cm^{-1}$ to 1778 $cm^{-1}$ in about 10 minutes. Fifty ml of toluene was added and the mixture was stirred overnight with 20 g of activated acidic alumina. The filtered mixture was stripped for 2 hours at 75° C. and 0.3 mm Hg to yield 92 g of red, viscous syrup.

Example C

Synthesis of SPH-Glycidol Reaction Product (4-oxo-4-(2-phenylhydrazinyl)butanoic acid) ("SPH") and glycidol were reacted in the presence of acetonitrile in amounts and the manner described below to form a reaction product (adduct), which can be used as an anaerobic cure accelerator. The reaction product was prepared in accordance with the synthetic scheme depicted below from the reactants set forth in Table 2:

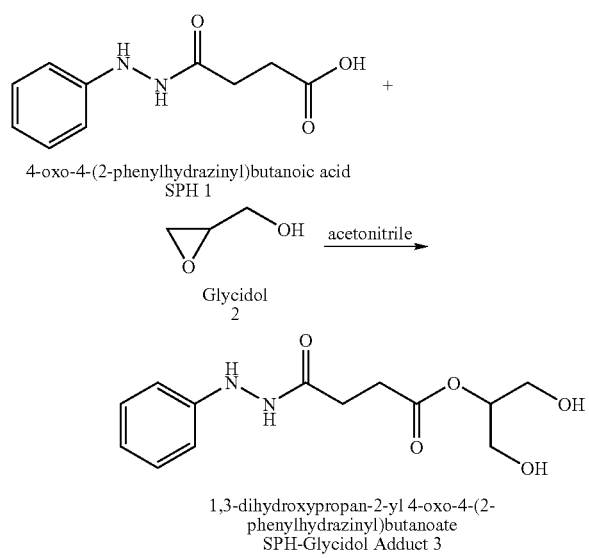

4-oxo-4-(2-phenylhydrazinyl)butanoic acid SPH 1

Glycidol 2

1,3-dihydroxypropan-2-yl 4-oxo-4-(2-phenylhydrazinyl)butanoate
SPH-Glycidol Adduct 3

TABLE 2

Reagents and Materials:

| Reagent | SPH | Glycidol | Acetonitrile | Adduct |
|---|---|---|---|---|
| C.A.S. No. | x | 556-52-5 | 75-05-8 | x |
| Molecular Weight (g/mole) | 208.21 | 74.08 | 41.05 | 282.29 |
| % Active | x | 96 | 99 | x |
| Density g/ml | x | 1.12 @ 25° C. | 0.79 | x |
| | | | | Theoretical Yield |
| Amount (g) | 3.00 | 1.54 | 50 ml | 4.07 |
| mmols | 14.41 | 20.00 | | 14.41* |

*97.8% of theoretical yield was obtained.

Figure 2:
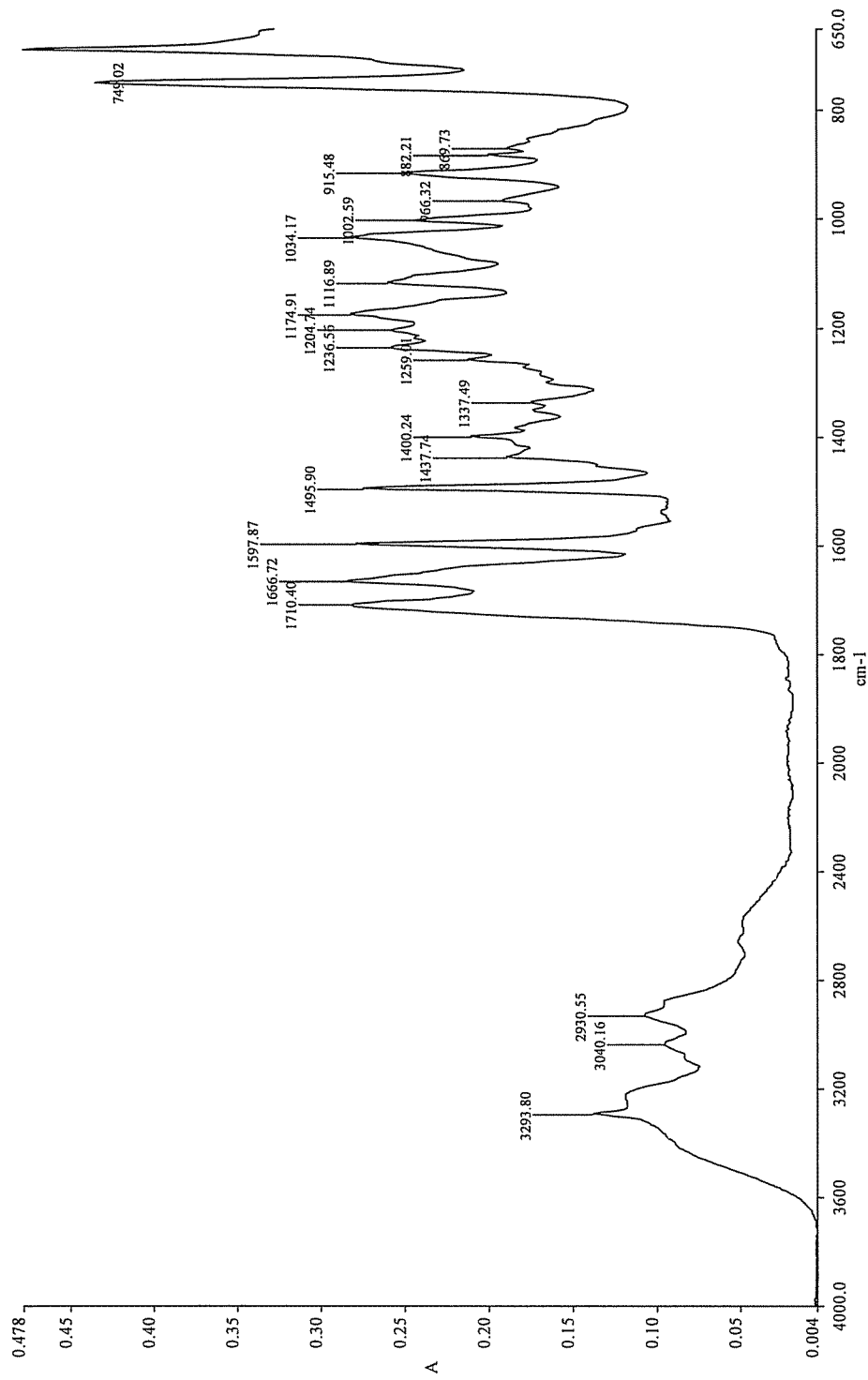
FIG. 2 depicts an IR spectra of an SPH-glycidol reaction product of Example C according to the present invention.

To a 3 neck 100 ml round bottom equipped with magnetic stirring, a reflux condenser, pressure equilibrated addition funnel, nitrogen purge and thermo-probe was added SPH (liquid 1) (3.00 g, 14.41 mmol), followed by the solvent acetonitrile (50 ml). The white suspension was warmed to 60° C., then the glycidol was added. The suspension clarified as it was stirred over the weekend at 60° C. An aliquot was taken and analyzed by Infrared ("IR") spectral analysis using a Perkin Elmer FT-IR to confirm structure. The clear pale amber liquid was concentrated in vacuo at 40° C. to a pale brown solid. The solid was further dried in vacuo at 50° C. The dried SPH-Glycidol Adduct was a light brown solid (3.98 g, 97.8% of theoretical yield). The solid was evaluated by $^1$H NMR, $^{13}$C NMR and FT-IR. The results of FT-IR analysis of the SPH-glycidol reaction product is shown in FIG. 2. $^1$H NMR: (DMSO-d6, 300 MHz) δ 9.95, 9.65, 7.1, 6.7, 5.1, 4.05, 3.9, 3.7, 3.4, 2.7, 2.6, 2.4. $^{13}$C NMR (DMSO-d6, 75 MHz) δ 175.0, 172.0, 150.0, 130.0, 119.0, 113.0, 77.0, 69.0, 64.0, 29.5, and 29.0.

Preparation of Anaerobic Curable Compositions

Selected components were premixed prior to mixing with the remaining components of the anaerobic base composition, as follows:

| Premix A: | |
|---|---|
| Component | % by weight |
| Polyethylene glycol dimethacrylate | 95 |
| Phenolic Stabilizer | 5 |

The components of Premix A were mixed by conventional stirring at about 25° C.

| Premix B: | |
|---|---|
| Component | % by weight |
| Propylene glycol | 73.5 |
| Water (deionized) | 23 |
| Chelating agent | 3.5 |

The components of Premix B were mixed by conventional stirring at about 25° C.

Premixes A and B were used to prepare the Formulation according to Table 3 as follows:

TABLE 3

| Material | Generic Description | A part | B part | C part |
|---|---|---|---|---|
| Polyethylene glycol (PEG) dimethacrylate | Dimethacrylate Monomer | 57.36 | 57.36 | 57.36 |
| Premix A | Phenolic Stabilizer Premix | 0.20 | 0.20 | 0.20 |
| Premix B | Chelating Stabilizer Premix | 1.25 | 1.25 | 1.25 |
| Tetraethylene glycol di (2-ethylhexoate) | Plasticizer/Diluent | 28.74 | 28.56 | 28.89 |
| Polyvinyl acetate Beads | Viscosity Modifier | 5.00 | 5.00 | 5.00 |
| Polyethylene Powder | Viscosity Modifier | 3.00 | 3.00 | 3.00 |
| Aerosil R972 | Fumed Silica | 2.00 | 2.00 | 2.00 |
| Saccharin | Conventional Anaerobic Accelerator | 1.00 | 1.00 | 1.00 |
| Maleic acid | Maleic acid | 0.30 | 0.30 | 0.30 |
| Acetyl phenylhydrazine | Conventional Anaerobic Accelerator | 0.15 | 0.00 | 0.00 |
| Phenylhydrazide-Carbonate Adduct of Example A | Phenylhydrazide-Carbonate Adduct | 0.00 | 0.33 | 0.00 |
| Cumene hydroperoxide | Conventional Anaerobic Initiator | 1.00 | 1.00 | 1.00 |
| | | 100.00 | 100.00 | 100.00 |

The first seven components were mixed in the order listed in Table 3, except only 18.4 parts of tetraethylene glycol di(2-ethylhexoate) was used. The components were mixed using a stainless steel propeller-type mixer such that the components were dissolved. As the components were mixed, the thickener components slowly 'dissolved into' the formulation and thickened to form a mixture. Some components required additional mixing time (minimally overnight) to completely dissolve. The remainder of the tetraethylene glycol di(2-ethylhexoate) (10.34 parts) and the remaining components were added to the mixture and mixed as above. APH (150.18 g/mole) was included in Formulation A as an additional accelerator. The phenylhydrazine-glycerol carbonate adduct (MW=331.8 g/mole) of Example A was included in Formulation B as an additional accelerator. No accelerator was used in Formulation C (Control).

Physical Property Evaluation

A phenylhydrazine-glycerol carbonate adduct cure system (Formulation B) of the present invention was compared with the formulations containing conventional cure component APH (Formulation A) and the Control Formulation C (no additional accelerator) by 82° C. accelerated stability and adhesion tests on steel nut/bolt specimens.

Shelf Life Stability

The 82° C. stability of the formulations was determined according to an evaluation in which the formulation is judged to have acceptable shelf stability if the adhesive formulation remains liquid for 3 hours or longer at 82° C. Three specimens of each of the above Formulations A-C were evaluated at 82° C. As shown in Table 4, the samples of Formulation B of the present invention generally provided acceptable stability at 82° C.

TABLE 4

| Formulation | 82° C. Stability in minutes |
|---|---|
| A | >120 |
|   | >120 |
|   | >120 |
| B | >120 |
|   | >120 |
|   | >120 |
| C | <90 |
|   | <90 |
|   | <90 |

Fixture Times

Breakloose/prevail adhesion testing was performed according to ASTM D5649. Breakloose torque is the initial torque required to decrease or eliminate the axial load in a seated assembly. Prevailing torque, after initial breakage of the bond, is measured at any point during 360° rotation of the nut. Prevailing torque is normally determined at 180° rotation of the nut. Steel ⅜×16 nuts and bolts were degreased with 1,1,1-trichloroethylene, adhesive was applied to the bolt, and the nut was screwed onto the bolt with a steel collar as a spacer.

Figure 3:
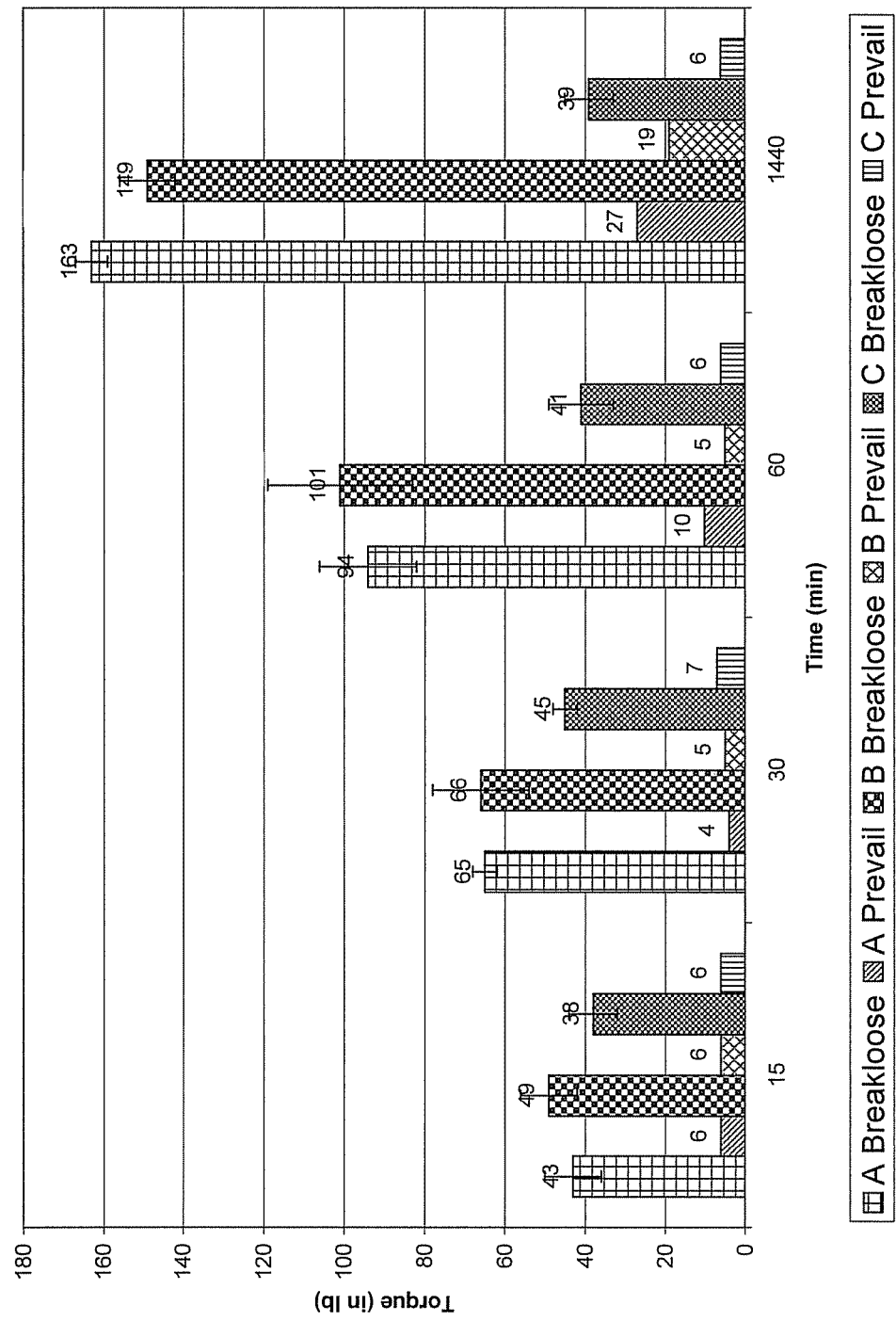
FIG. 3 depicts a bar chart of breakloose and prevailing torque on steel threaded fasteners of a control adhesive composition, an adhesive composition including conventional accelerator APH and an adhesive composition including a phenylhydrazine-glycerol carbonate reaction product according to the present invention.

Twenty nut and bolt specimens were assembled for each adhesive formulation tested. For the break/prevail adhesion tests, the specimens were maintained at ambient temperature for 15 minutes, 30 minutes, 1 hour and 24 hours after assembly (five specimens each). The break and prevail torque strengths (in-lb$_f$) were then recorded for five specimens of each adhesive formulation after 15 minutes, 30 minutes, one hour and after 24 hours at ambient temperature (25° C.) and 45-50% relative humidity, respectively. The torque strengths were measured using a calibrated automatic torque analyzer. The data for these evaluations is set forth below in Table 5 and FIG. 3.

This data indicates that Formulation B in accordance with this invention exhibited similar breakloose and prevail properties at room temperature compared to traditional anaerobic (meth)acrylate-based adhesives when applied and cured on the substrates.

TABLE 5

| | | Breakloose/180 Prevail (in lbs) | | | | | | | |
|---|---|---|---|---|---|---|---|---|---|
| | | 15 minutes | | 30 minutes | | 1 Hour 60 | | 24 Hour 1440 | |
| | | 15 | | 30 | | 180 | | 180 | |
| Formula | | Break | 180 Prevail | Break | 180 Prevail | Break | Prevail | Break | Prevail |
| A | +/− | 43 | 6 | 65 | 4 | 94 | 10 | 163 | 27 |
| | | 7 | 0 | 3 | 1 | 12 | 17 | 4 | 7 |
| B | +/− | 49 | 6 | 66 | 5 | 101 | 5 | 149 | 19 |
| | | 7 | 0 | 12 | 1 | 18 | 1 | 7 | 6 |
| C | +/− | 38 | 6 | 45 | 7 | 41 | 6 | 39 | 6 |
| | | 6 | 0 | 3 | 0 | 8 | 1 | 6 | 0 |

Adhesive Example 2

Adhesive formulations were prepared in a manner similar to Adhesive Example 1 as set forth in Table 6 below. APH (150.18 g/mole) was included in Formulation A as an additional accelerator. The phenylhydrazine-glycerol carbonate adduct (MW=331.8 g/mole) of Example B above:

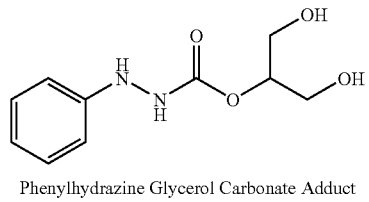 [SMILES: O=C(NNc1ccccc1)OC(CO)CO]

Phenylhydrazine Glycerol Carbonate Adduct was included in Formulation B as an additional accelerator. No additional accelerator was used in Formulation C (Control).

TABLE 6

| Material | Generic Description | A part | B part | C part |
|---|---|---|---|---|
| Polyethylene glycol (PEG) dimethacrylate | Dimethacrylate Monomer | 57.36 | 57.36 | 57.36 |
| Premix A | Phenolic Stabilizer Premix | 0.20 | 0.20 | 0.20 |
| Premix B | Chelating Stabilizer Premix | 1.25 | 1.25 | 1.25 |
| Tetraethylene glycol di (2-ethylhexoate) | Plasticizer/Diluent | 28.74 | 28.56 | 28.89 |
| Polyvinyl acetate Beads | Viscosity Modifier | 5.00 | 5.00 | 5.00 |
| Polyethylene Powder | Viscosity Modifier | 3.00 | 3.00 | 3.00 |
| Aerosil R972 | Fumed Silica | 2.00 | 2.00 | 2.00 |

TABLE 6-continued

| Material | Generic Description | A part | B part | C part |
|---|---|---|---|---|
| Saccharin | Conventional Anaerobic Accelerator | 1.00 | 1.00 | 1.00 |
| Maleic acid | Maleic acid | 0.30 | 0.30 | 0.30 |
| Acetyl phenylhydrazine | Conventional Anaerobic Accelerator | 0.15 | 0.00 | 0.00 |
| Phenylhydrazide-Carbonate Adduct of Example B | Phenylhydrazide-Carbonate Adduct | 0.00 | 0.33 | 0.00 |
| Cumene hydroperoxide | Conventional Anaerobic Initiator | 1.00 | 1.00 | 1.00 |
|  |  | 100.00 | 100.00 | 100.00 |

Physical Property Evaluation

A phenylhydrazine-glycerol carbonate adduct cure system (Formulation B) of the present invention was compared with the formulations containing conventional cure component APH (Formulation A) and the Control Formulation C (no additional accelerator) by 82° C. accelerated stability and adhesion tests on steel nut/bolt specimens.

Shelf Life Stability

The 82° C. stability of the formulations was determined according to an evaluation in which the formulation is judged to have acceptable shelf stability if the adhesive formulation remains liquid for 3.5 hours or longer at 82° C. Three specimens of each of the above Formulations A-C were evaluated at 82° C. As shown in Table 7, the samples of Formulation B of the present invention generally provided acceptable stability at 82° C.

TABLE 7

| Formulation | 82° C. Stability in minutes |
|---|---|
| A | >180 |
|  | >180 |
|  | >180 |
| B | <180 |
|  | >180 |
|  | >180 |
| C | <120 |
|  | <150 |
|  | <120 |

Fixture Times

Breakloose/prevail adhesion testing was performed according to ASTM D5649. Breakloose torque is the initial torque required to decrease or eliminate the axial load in a seated assembly. Prevailing torque, after initial breakage of the bond, is measured at any point during 360° rotation of the nut. Prevailing torque is normally determined at 180° rotation of the nut. Steel ⅜×16 nuts and bolts were degreased with 1,1,1-trichloroethylene, adhesive was applied to the bolt, and the nut was screwed onto the bolt with a steel collar as a spacer.

Figure 4:
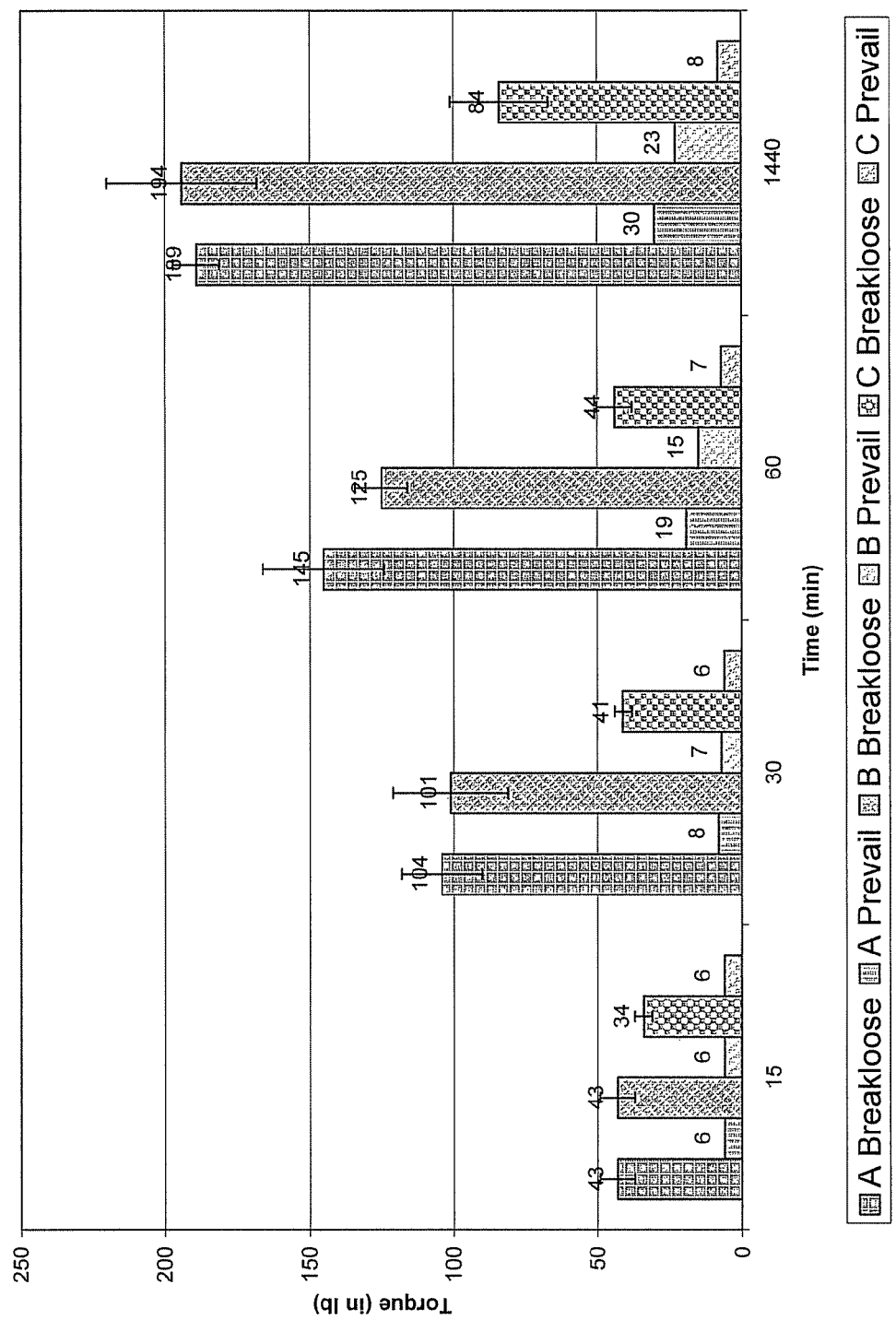
FIG. 4 depicts a bar chart of breakloose and prevailing torque on steel threaded fasteners of a control adhesive composition, an adhesive composition including conventional accelerator APH and an adhesive composition including a phenylhydrazine-glycerol carbonate reaction product according to the present invention.

Twenty nut and bolt specimens were assembled for each adhesive formulation tested. For the break/prevail adhesion tests, the specimens were maintained at ambient temperature for 15 minutes, 30 minutes, 1 hour and 24 hours after assembly (five specimens each). The break and prevail torque strengths (in-lb$_f$) were then recorded for five specimens of each adhesive formulation after 15 minutes, 30 minutes, one hour and after 24 hours at ambient temperature (25° C.) and 45-50% relative humidity, respectively. The torque strengths were measured using a calibrated automatic torque analyzer. The data for these evaluations is set forth below in Table 8 and FIG. 4.

This data indicates that Formulation B in accordance with this invention exhibited similar breakloose and prevail properties at room temperature compared to traditional anaerobic (meth)acrylate-based adhesives when applied and cured on the substrates.

TABLE 8

| | | Breakloose/180 Prevail (in lbs) | | | | | | |
|---|---|---|---|---|---|---|---|---|
| | | 15 minutes | | 30 minutes | | 1 Hour 60 | | 24 Hour 1440 |
| | | 15 | | 30 | | 180 | | 180 |
| Formula | | Break | 180 Prevail | Break | 180 Prevail | Break | Prevail | Break | Prevail |
| A | +/− | 43 | 6 | 104 | 8 | 145 | 19 | 189 | 30 |
|  |  | 6 | 0 | 14 | 5 | 21 | 3 | 8 | 9 |
| B | +/− | 43 | 6 | 101 | 7 | 125 | 15 | 194 | 23 |
|  |  | 6 | 0 | 20 | 7 | 9 | 8 | 26 | 11 |
| C | +/− | 34 | 6 | 41 | 6 | 44 | 7 | 84 | 8 |
|  |  | 3 | 0 | 3 | 0 | 6 | 0 | 17 | 3 |

What is claimed is:

1. A compound selected from the group of compounds represented by structural Formula (I):

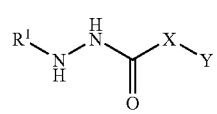

Formula (I)

wherein in Formula I:
R$^1$ is selected from the group consisting of aryl and heteroaryl;
X is selected from the group consisting of —O—, —S—, —NH—, cycloalkylene, heterocyclylene, arylene, alkarylene, and heteroarylene;
Y is a substituted alkylene group comprising an alkylene backbone having at least two contiguous carbon atoms and which optionally can be interrupted by one or more —O—, —S—, or —NH— moieties,
provided that each —O—, —S—, or —NH— moiety of Y, if present, is not adjacent to an —O—, —S—, or —NH— of X,
wherein the alkylene group of Y has substituents which are independently selected from the group consisting of —OH, —NH$_2$, —SH, cycloalkyl, heterocyclyl, aryl, and heteroaryl, or two hydrogen atoms on the same carbon atom of Y are replaced by carbonyl, and
wherein at least two substituents of Y are each independently selected from the group consisting of —OH, —NH$_2$, and —SH, and provided that each of the —OH, —NH₂, or —SH groups is not attached to the same carbon atom of Y or an —O—, —S—, or —NH— backbone moiety of Y, and provided that Y has less than three —OH substituents.

2. The compound according to claim 1, wherein X is —O—.

3. The compound according to claim 1, wherein Y comprises two —OH substituents.

4. The compound according to claim 1, wherein the compound is represented by structural Formula (A):

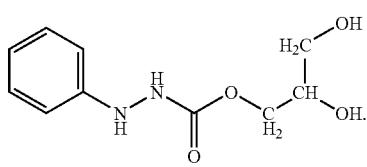

Formula (A)

5. The compound according to claim 1 wherein the compound is represented by structural Formula (B):

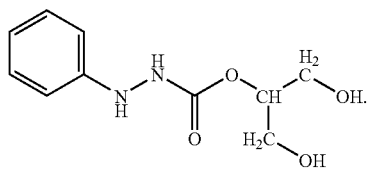

Formula (B)

6. A compound represented by structural Formula (C):

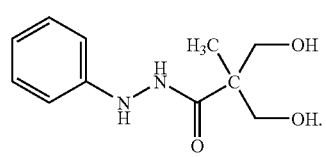

Formula (C)

7. A composition comprising the compound of claim 1.

8. A reaction product prepared from reactants comprising:

a) at least one compound selected from the group of compounds represented by structural Formula (II)

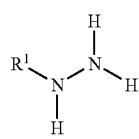

Formula (II)

wherein in Formula II:

R¹ is selected from the group consisting of aryl and heteroaryl; and b) a compound selected from the group of compounds represented by structural Formula (III) or structural Formula (IV):

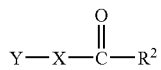

Formula (III)

wherein in Formula III:

X is selected from the group consisting of —O—, —S—, —NH—, cycloalkylene, heterocyclylene, arylene, alkarylene, and heteroarylene;

Y is a substituted alkylene group comprising an alkylene backbone having at least two contiguous carbon atoms and which optionally can be interrupted by one or more —O—, —S—, or —NH— moieties, provided that each —O—, —S—, or —NH— moiety of Y, if present, is not adjacent to an —O—, —S—, or —NH— of X, wherein the alkylene group of Y has substituents which are independently selected from the group consisting of —OH, —NH₂, —SH, cycloalkyl, heterocyclyl, aryl, and heteroaryl, or two hydrogen atoms on the same carbon atom of Y are replaced by carbonyl, and wherein at least two substituents of Y are each independently selected from the group consisting of —OH, —NH₂, and —SH, and provided that each of the —OH, —NH₂, or —SH groups is not attached to the same carbon atom of Y or an —O—, —S—, or —NH— backbone moiety of Y, and provided that Y has less than three —OH substituents; and R² is selected from the group consisting of —OR, —NHR, alkyl, and arylalkyl, wherein R is H, alkyl or arylalkyl; and

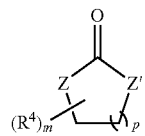

Formula (IV)

wherein in Formula IV:

Z and Z' are each independently selected from the group consisting of —O—, —S—, and —N(R³)—, wherein R³ is H or alkyl;

m is at least 1;

each R⁴ is independently selected from the group consisting of hydroxyalkyl, aminoalkyl, thioalkyl, hydroxyl substituted cycloalkyl, arylalkyl having at least one —OH, —NH₂, or —SH group, and heteroarylalkyl having at least one —OH, —NH₂, or —SH group, provided that there is no more than one R⁴ substituent attached to a substitutable ring carbon atom; and p is 1 or 2, wherein the reaction product comprises at least one compound selected from the group of compounds represented by structural Formula (I):

Formula (I)

[Structure: R⁵–NH–NH–C(=O)–W–M']

wherein in Formula I:
R⁵ is selected from the group consisting of aryl and heteroaryl;
W is selected from the group consisting of —O—, —S—, —NH—, cycloalkylene, heterocyclylene, arylene, alkarylene, and heteroarylene;
M' is a substituted alkylene group comprising an alkylene backbone having at least two contiguous carbon atoms and which optionally can be interrupted by one or more —O—, —S—, or —NH— moieties,
provided that each —O—, —S—, or —NH— moiety of M', if present, is not adjacent to an —O—, —S—, or —NH— of W,
wherein the alkylene group of M' has substituents which are independently selected from the group consisting of —OH, —NH₂, —SH, cycloalkyl, heterocyclyl, aryl, and heteroaryl, or two hydrogen atoms on the same carbon atom of M' are replaced by carbonyl, and
wherein at least two substituents of M' are each independently selected from the group consisting of —OH, —NH₂, and —SH, and
provided that each of the —OH, —NH₂, or —SH groups is not attached to the same carbon atom of M' or an —O—, —S—, or —NH— backbone moiety of M', and provided that M' has less than three —OH substituents.

9. The reaction product according to claim 8, wherein R¹ is phenyl.

10. The reaction product according to claim 8, wherein X is —O—.

11. The reaction product according to claim 8, wherein Y comprises two —OH substituents.

12. The reaction product according to claim 8, wherein R⁴ is hydroxyalkyl.

13. The reaction product according to claim 8, wherein the compound of formula II is

[Structure: phenyl-NH-NH-NH₂ type hydrazine]

14. The reaction product according to claim 8, wherein the compound of Formula IV is

[Structure: glycidol carbonate — cyclic carbonate with CH₂OH substituent]

15. A composition comprising the reaction product of claim 8.

16. The reaction product according to claim 8, wherein the reaction product is a composition represented by structural formula A:

Formula (A)

[Structure showing phenyl-NH-NH-C(=O)-O-CH₂-CH(OH)-CH₂OH]

17. The reaction product according to claim 8, wherein the reaction product is a composition represented by structural formula B:

Formula (B)

[Structure showing phenyl-NH-NH-C(=O)-O-CH(CH₂OH)-CH₂OH]

18. The reaction product according to claim 8, wherein the reaction product comprises a mixture of at least one compound represented by structural Formula (A):

Formula (A)

[Structure as above for Formula A]

and at least one compound represented by structural Formula (B):

Formula (B)

[Structure as above for Formula B]

19. A reaction product prepared from reactants comprising:
a) at least one compound selected from the group of compounds represented by structural Formula (V):

Formula (V)

[Structure: phenyl-NH-NH-C(=O)-R⁵]

wherein in Formula V:

R⁵ is selected from the group consisting of hydroxyalkyl and carboxyalkyl; and b) at least one compound selected from the group of compounds represented by structural Formula (VI):

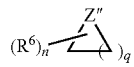

Formula (VI)

wherein in Formula VI:

Z" is selected from the group consisting of —O—, —S—, and —NH—;

q is 1 to 4;

R⁶ is independently selected from the group consisting of hydroxyalkyl, aminoalkyl, and thioalkyl; and n is at least 1, wherein the reaction product comprises at least one compound of structural Formula (D1) or (D2):

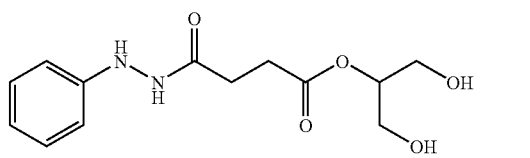

Formula (D1)

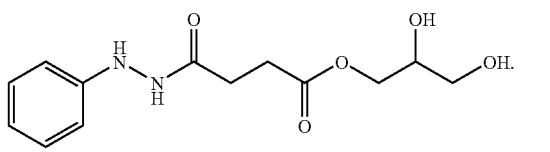

Formula (D2)

20. The reaction product according to claim 19, wherein the compound of Formula V is

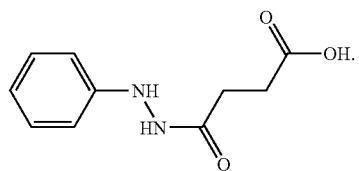

21. The reaction product according to claim 19, wherein the compound of Formula VI is

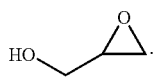

22. A method of making a compound selected from the group of compounds represented by structural Formula (I):

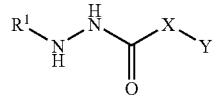

Formula (I)

wherein in Formula I:

R¹ is selected from the group consisting of aryl and heteroaryl;

X is selected from the group consisting of —O—, —S—, —NH—, cycloalkylene, heterocyclylene, arylene, alkarylene, and heteroarylene;

Y is a substituted alkylene group comprising an alkylene backbone having at least two contiguous carbon atoms which optionally can be interrupted by an —O—, —S—, or —NH-moiety, provided that the —O—, —S—, or —NH— of Y, if present, is not adjacent to another —O—, —S—, or —NH— group of X, wherein the alkylene group has substituents which are independently selected from the group consisting of —OH, —NH₂, —SH, cycloalkyl, heterocyclyl, aryl, and heteroaryl, or two hydrogen atoms on the same carbon atom of Y are replaced by carbonyl, and wherein at least two substituents are each independently selected from the group consisting of —OH, —NH₂, and —SH, and provided that each of the —OH, —NH₂, or —SH is not attached to the same carbon atom of Y or an —O—, —S—, or —NH— backbone moiety of Y, and provided that Y has less than three —OH substituents, comprising the step of reacting:

(a) at least one compound selected from the group of compounds represented by structural Formula (II):

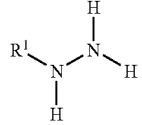

Formula (II)

wherein in Formula II:

R¹ is selected from the group consisting of aryl and heteroaryl; with (b) a compound selected from the group of compounds represented by structural Formula (III) or structural Formula (IV):

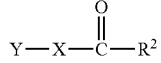

Formula (III)

wherein in Formula III:

X is selected from the group consisting of —O—, —S—, —NH—, cycloalkylene, heterocyclylene, arylene, alkarylene, and heteroarylene;

Y is a substituted alkylene group comprising an alkylene backbone having at least two contiguous carbon atoms which optionally can be interrupted by —O—, —S—, or —NH-moieties, provided that the —O—, —S—, or —NH— of Y, if present, is not adjacent to another —O—, —S—, or —NH— group of X, wherein the alkylene group has substituents which are independently selected from the group consisting of —OH, —NH₂, —SH, cycloalkyl, heterocyclyl, aryl, and heteroaryl, or two hydrogen atoms on the same carbon atom of Y are replaced by carbonyl, and wherein at least two substituents are each independently selected from the group consisting of —OH, —NH$_2$, and —SH, and provided that each of the —OH, —NH$_2$, or —SH is not attached to the same carbon atom of Y or an —O—, —S—, or —NH— backbone moiety of Y; and R$^2$ is selected from the group consisting of —OR, NHR, alkyl, and arylalkyl, wherein R is H, alkyl or arylalkyl; and

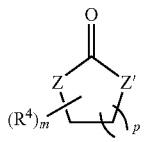

Formula (IV)

wherein in Formula IV:

Z and Z' are each independently selected from the group consisting of —O—, —S—, and —N(R$^3$)—, wherein R$^3$ is H or alkyl;

m is at least 1;

each R$^4$ is independently selected from the group consisting of hydroxyalkyl, aminoalkyl, thioalkyl, hydroxyl substituted cycloalkyl, arylalkyl having at least one —OH, —NH$_2$, or —SH group, and heteroarylalkyl having at least one —OH, —NH$_2$, or —SH group, provided that there is no more than one R$^4$ substituent attached to a substitutable ring carbon atom; and p is 1 or 2.

* * * * *